United States Patent
Chen et al.

(10) Patent No.: US 12,076,145 B2
(45) Date of Patent: Sep. 3, 2024

(54) LACTATE SENSORS AND ASSOCIATED METHODS

(71) Applicant: Abbott Diabetes Care Inc., Alameda, CA (US)

(72) Inventors: Kuan-Chou Chen, Fremont, CA (US); Tianmei Ouyang, Fremont, CA (US); Stephen Oja, Alameda, CA (US); Benjamin Feldman, Berkeley, CA (US); Hyun Cho, Berkeley, CA (US); Lam Tran, Dublin, CA (US); Mark Eshoo, San Diego, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 153 days.

(21) Appl. No.: 16/259,157

(22) Filed: Jan. 28, 2019

(65) Prior Publication Data

US 2019/0320947 A1      Oct. 24, 2019

Related U.S. Application Data

(60) Provisional application No. 62/797,566, filed on Jan. 28, 2019, provisional application No. 62/659,761, (Continued)

(51) Int. Cl.
*A61B 5/1486* (2006.01)
*A61B 5/145* (2006.01)
*G01N 27/327* (2006.01)

(52) U.S. Cl.
CPC ........ *A61B 5/1486* (2013.01); *A61B 5/14532* (2013.01); *A61B 5/14539* (2013.01); (Continued)

(58) Field of Classification Search
CPC .............. A61B 5/1486; A61B 5/14503; A61B 5/14532; A61B 5/14539; A61B 5/14546; G01N 27/3271
See application file for complete search history.

(56) References Cited

U.S. PATENT DOCUMENTS 6,134,461 A     10/2000 Say et al.
6,605,200 B1    8/2003 Mao et al.
(Continued)

FOREIGN PATENT DOCUMENTS

AU    2010337426 A1 *  7/2012  ............. A61B 5/412
JP    2001520367 A     10/2001
(Continued)

OTHER PUBLICATIONS

Romero, Marcelo Ricardo, Et. Al. "Design and optimization of a lactate amperometric biosensor based on lactate oxidase cross-linked with polymeric matrixes" May 14, 2008, Sensors and Actuators, 131:2, 590-595 (Year: 2008).*
(Continued)

*Primary Examiner* — May A Abouelela
*Assistant Examiner* — Anna Roberts
(74) *Attorney, Agent, or Firm* — Sterne, Kessler, Goldstein & Fox P.L.L.C.

(57) ABSTRACT

A lactate-responsive enzyme may form the basis for lactate detection and quantification using an electrochemical analyte sensor. Various features may be incorporated within an analyte sensor containing a lactate-responsive enzyme, particularly lactate oxidase, to improve sensitivity and response stability of the analyte sensor. Such analyte sensors may comprise: a working electrode having an active area disposed thereon, and a mass transport limiting membrane overcoating at least the active area upon the working electrode. The active area comprises at least a polymer, an
(Continued)

albumin, and a lactate-responsive enzyme that is covalently bonded to the polymer. The mass transport limiting membrane may comprise at least a crosslinked polyvinylpyridine homopolymer or copolymer. The analyte sensors may determine a lactate concentration in a biological fluid, particularly in vivo, which may be correlated to various physiological conditions.

35 Claims, 9 Drawing Sheets

Related U.S. Application Data filed on Apr. 19, 2018, provisional application No. 62/659,759, filed on Apr. 19, 2018.

(52) U.S. Cl.
CPC ...... *A61B 5/14546* (2013.01); *A61B 5/14503* (2013.01); *G01N 27/3271* (2013.01)

(56) References Cited

U.S. PATENT DOCUMENTS

| | | |
|---|---|---|
| 6,605,201 B1 | 8/2003 | Mao et al. |
| 6,736,957 B1 | 5/2004 | Forrow et al. |
| 7,501,053 B2 | 3/2009 | Karinka et al. |
| 7,754,093 B2 | 7/2010 | Forrow et al. |
| 8,268,143 B2 | 9/2012 | Liu et al. |
| 8,444,834 B2 | 5/2013 | Liu et al. |
| 9,914,952 B2 | 3/2018 | Ouyang et al. |
| 10,136,816 B2 | 11/2018 | Bernstein et al. |
| 2003/0042137 A1* | 3/2003 | Mao ............... C12Q 1/006 204/415 |
| 2005/0215871 A1* | 9/2005 | Feldman ............ C12Q 1/002 204/403.01 |
| 2006/0004272 A1 | 1/2006 | Shah et al. |
| 2008/0319296 A1* | 12/2008 | Bernstein ......... A61B 5/1495 600/365 |
| 2010/0025238 A1* | 2/2010 | Gottlieb ........... A61B 5/14532 204/401 |
| 2010/0331643 A1* | 12/2010 | Mazza ............. A61B 5/14532 600/345 |
| 2012/0132525 A1* | 5/2012 | Liu .................. C07F 15/0026 525/327.1 |
| 2017/0191955 A1* | 7/2017 | Zou ................. A61B 5/14546 |
| 2017/0315077 A1 | 11/2017 | Rao et al. |
| 2018/0263539 A1* | 9/2018 | Javey .............. A61B 5/1477 |

FOREIGN PATENT DOCUMENTS

| | | |
|---|---|---|
| JP | 2005520172 A | 7/2005 |
| JP | 2010530790 A | 9/2010 |
| JP | 2013543405 A | 12/2013 |
| WO | WO-1999019507 A1 | 4/1999 |
| WO | WO-2004058992 A1 | 7/2004 |
| WO | WO-2008118257 A1 | 10/2008 |
| WO | WO-2008157820 A1 | 12/2008 |
| WO | WO-2012045425 A1 | 4/2012 |
| WO | WO-2016049243 A1 | 3/2016 |

OTHER PUBLICATIONS

Rong, Zimei et al. "Needle Enzyme Electrode for Lactate Measurement In Vivo" Jan. 2008, IEEE Sensors Journal, vol. 8, No. 1 (Year: 2008).*

Monosik, R., et al., "Application of Enzyme Biosensors in Analysis of Food and Beverages," *Food Analytical Methods* 5:40-53, Springer New York, United States (2012).

\* cited by examiner

LACTATE SENSORS AND ASSOCIATED METHODS

CROSS-REFERENCE TO RELATED APPLICATIONS

The present application claims the benefit of priority under 35 U.S.C. § 119 from U.S. Provisional Patent applications 62/659,759 and 62/659,761, each filed on Apr. 19, 2018, and U.S. Provisional Patent application 62/797,566 filed on Jan. 28, 2019, each of which is incorporated herein by reference in its entirety.

STATEMENT REGARDING FEDERALLY SPONSORED RESEARCH OR DEVELOPMENT

Not applicable.

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental factors or stimuli. Glucose levels, for example, can be particularly important to detect and monitor in diabetic individuals.

Lactate is another analyte whose in vivo levels may vary in response to numerous environmental or physiological factors including, for example, eating, stress, exercise, sepsis or septic shock, infection, hypoxia, presence of cancerous tissue, and the like. In the case of chronic lactate-altering conditions (e.g., disease), lactate levels may change slowly, such that they may be readily quantified using conventional blood draws and laboratory measurements. Other lactate-altering conditions may be episodic in nature, in which case lactate levels may fluctuate very rapidly and irregularly. Conventional laboratory measurements may be ill suited to determine lactate levels in such instances. Namely, lactate levels may have changed several times between successive measurements, and an abnormal lactate level may be completely missed in such instances, thereby leading to potentially incorrect diagnoses. In the case of rapidly fluctuating lactate levels, it can be desirable to measure an individual's lactate levels continuously, such as through using an implanted in vivo lactate sensor. Continuous lactate monitoring can also be advantageous in individuals with chronic, slowly changing lactate levels as well. For example, continuous lactate monitoring can avoid the pain and expense associated with conducting multiple blood draws for assaying lactate levels.

Continuous analyte monitoring using an implanted sensor can be advantageous in some instances, but there are certain challenges associated with these types of measurements. Intravenous analyte sensors are invasive and can sometimes be painful for an individual to wear, particularly over an extended period. Subcutaneous, interstitial, or dermal analyte sensors can often be less painful for an individual to wear and can provide sufficient measurement accuracy in many cases.

Non-intravenous in vivo glucose-responsive analyte sensors have been developed over the past two decades by several manufacturers, and some have recently gained regulatory approval for monitoring glucose levels in diabetic individuals. Such glucose-responsive analyte sensors employ glucose oxidase that is covalently bound to a polymer to facilitate glucose detection and to a transition metal complex (electron transfer agent or electron transfer mediator) to aid in conveyance of electrons released during the oxidation of glucose. In vivo glucose-responsive analyte sensors available from other manufacturers also employ glucose oxidase as the basis for sensing but vary the sensing chemistry/protocol in various ways.

In vivo analyte sensors for assaying glucose and other analytes may include a membrane disposed over at least the implanted portion of the analyte sensor. In one aspect, the membrane may improve biocompatibility of the analyte sensor. In another aspect, the membrane may be permeable or semi-permeable to an analyte of interest and limit the overall analyte flux to the active area of the analyte sensor, such that the membrane functions as a mass transport limiting membrane. Limiting analyte access to the active area of the analyte sensor with a mass transport limiting membrane can aid in avoiding sensor overload (saturation), thereby improving detection performance and accuracy. Such membranes may be highly specific toward limiting mass transport of a particular analyte, with other substances permeating through the membrane at significantly different rates. As such, it may be challenging to identify a membrane polymer suitable to incorporate in a mass transport limiting membrane for a given analyte, such as lactate, that affords high analyte sensitivity and a stable sensor response.

Functional lactate-responsive analyte sensors may be constructed by replacing the glucose oxidase from a glucose-responsive analyte sensor with lactate oxidase. Unlike the glucose-responsive analyte sensors discussed in brief above, the corresponding lactate-responsive analyte sensors generally display inferior performance for assaying lactate using similar sensing chemistry. Namely, the direct replacement of glucose oxidase with lactate oxidase may afford a lactate-responsive analyte sensor with poor sensitivity and/or an insufficiently stable sensor response. Thus, lactate-responsive analyte sensors, although functional, have not yet reached a level of development to provide stable, high-sensitivity lactate analyses. As such, the diagnostic value of lactate-responsive analyte sensors remains fairly limited, despite the wealth of potential information that may be gained through monitoring lactate.

As previously referenced, lactate-responsive analyte sensors may replace glucose oxidase with lactate oxidase to facilitate lactate detection. Such lactate-responsive analyte sensors based upon modified glucose-responsive sensor chemistry are described in commonly owned U.S. Pat. No. 9,914,952, which is incorporated herein by reference in its entirety. As described therein, enhancement of the analytical sensitivity toward lactate and some response stabilization may be realized by modifying the glucose-responsive sensor chemistry to include catalase in the active area when lactate oxidase is instead present. Although the incorporation of catalase helps to some degree, it does not completely stabilize the long-term response of the analyte sensor. Instead, the lactate signal in catalase-containing analyte sensors falls up to about 10% over 48 hours of monitoring. Since catalases are known to be reactive toward hydrogen peroxide, the stabilization effect of catalase in lactate-responsive analyte sensors is believed to involve scrubbing of transient hydrogen peroxide that may otherwise impact the activity of the lactate oxidase. Although catalase may improve the performance of lactate-responsive analyte sensors, additional performance improvement may still be needed for such analyte sensors to realize their true potential.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
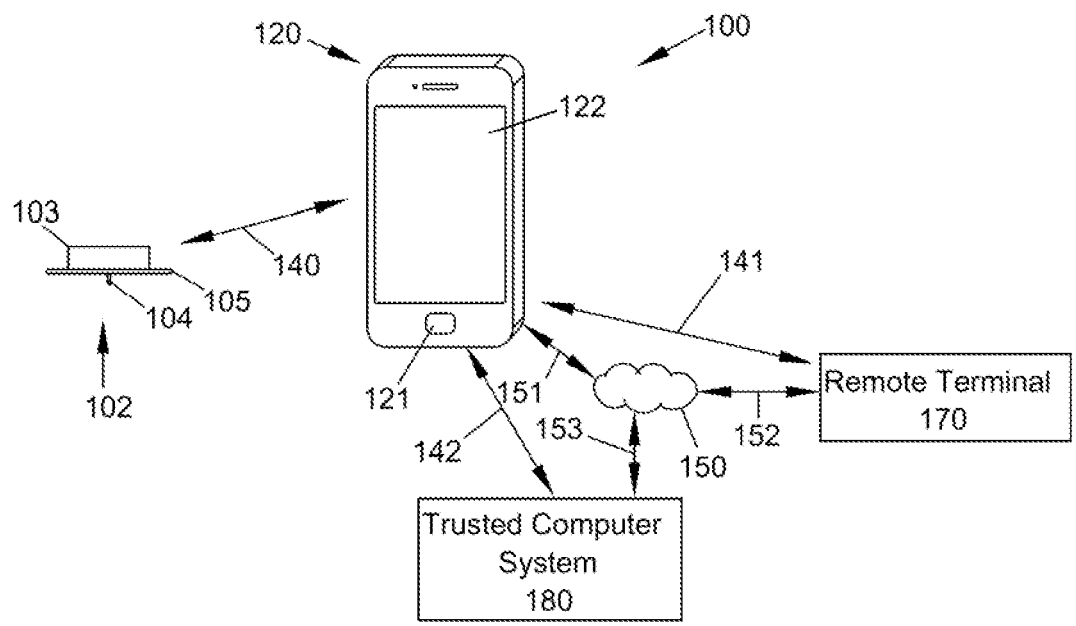
FIG. 1 shows a diagram of an illustrative sensing system that may incorporate an analyte sensor of the present disclosure.

The present disclosure generally describes lactate-responsive analyte sensors and methods employing such analyte sensors and, more specifically, lactate-responsive analyte sensors and methods affording high sensitivity and stable responsiveness toward lactate.

As discussed above, measurement of lactate levels (concentrations) may be diagnostic of various physiological conditions and/or exposure to certain environmental factors. Although laboratory measurements of lactate concentrations may be sufficient to monitor some physiological conditions, lactate levels may fluctuate too rapidly in other instances for laboratory measurements to be feasible. In vivo lactate-responsive analyte sensors employing a lactate-responsive enzyme may be used to conveniently assay both slowly and rapidly fluctuating lactate concentrations, which may afford particular diagnostic advantages for monitoring various conditions in which lactate concentrations rapidly and/or unexpectedly fluctuate.

High analytical sensitivity and response stability are leading factors that may both be needed for satisfactory performance of analyte sensors, particularly those intended for extended in vivo use. Despite the potential benefits that may be realized by monitoring lactate levels in vivo, lactate-responsive analyte sensors having sufficient sensitivity and response stability for reliable diagnostic analyses have not yet been developed.

Although high sensitivity and response stability may be realized in glucose-responsive analyte sensors containing glucose oxidase, these desirable performance features do not presently translate to lactate-responsive analyte sensors upon the simple substitution of lactate oxidase for glucose oxidase. Namely, the sensitivity and response stability of a lactate-responsive analyte sensor is considerably poorer than a comparable glucose-responsive sensor. At least some of this difficulty is due to differences between glucose oxidase and lactate oxidase. Some progress has been made by utilizing a stabilizer (e.g., catalase) to improve the functionality of lactate-responsive analyte sensors, but desired levels of sensitivity and response stability have not yet been achieved.

In addition, the mass transport limiting membrane of lactate-responsive analyte sensors is a further source of difficulty. To date, the mass transport limiting membranes used successfully in glucose-responsive analyte sensors have afforded inferior sensing characteristics for assaying lactate using a lactate-responsive enzyme. Membrane polymers, or combinations thereof, that are more compatible with lactate have yet to be described.

The present disclosure describes concurrent approaches that may be utilized to improve the sensitivity and extended response stability of lactate-responsive analyte sensors. Improvement of these factors may provide high-quality analyte data over extended wear lifetimes spanning several days or more, ideally one week or more, which may be of significant diagnostic value. Namely, as discussed further herein, the performance of lactate-responsive analyte sensors may be improved by substituting a different stabilizer for catalase and by changing the mass transport limiting membrane disposed upon the active area. Several different membrane chemistries or configurations may promote improved analyte sensor performance for lactate analyses, as discussed herein.

First, the present disclosure substitutes a benign stabilizer for lactate oxidase that affords significant performance advantages compared to catalase. Namely, the present disclosure describes how serum albumin, particularly human serum albumin, may be incorporated within the active area of a lactate-responsive analyte sensor to promote response sensitivity (i.e., the magnitude of the observed sensor response). The terms "albumin" and "serum albumin" are used synonymously herein. Human serum albumin is the most abundant protein found in blood plasma. As such, there is not any apparent biocompatibility issue with introducing this stabilizer within an analyte sensor intended for in vivo human use. The suitability of human serum albumin as a replacement for catalase stabilizer is particularly surprising, since there is no known hydrogen peroxide clearance function associated with human serum albumin. Without being bound by theory or mechanism, this result suggests that catalase may function in a manner unrelated to its usual hydrogen peroxide clearance function in previous lactate-responsive analyte sensors. Other albumin proteins, such as bovine serum albumin, for example, may be similarly incorporated in a lactate-responsive analyte sensor to realize comparable advantages to those discussed herein.

Albumin proteins may present particular advantages over other types of proteinaceous stabilizers, such as catalase, in terms of their thermal stability. Some proteinaceous stabilizers may undergo denaturation, thereby leading to loss of their stabilizing functionality, upon being heated. Advantageously, albumin proteins do not readily denature upon being exposed to temperatures approaching 60° C., thereby allowing the albumin proteins to maintain their stabilizing functionality after thermal curing of the active sensor area takes place, as discussed further herein.

Although the incorporation of serum albumin in the active area of a lactate-responsive analyte sensor may improve sensor performance, particularly response sensitivity, it is usually insufficient alone to provide desired levels of both response sensitivity and extended response stability. Surprisingly, proper selection of the mass transport limiting membrane in a lactate-responsive analyte sensor may provide both sufficient lactate sensitivity and extended response stability, particularly when overcoating an active area comprising a serum albumin. In combination with a serum albumin in the active area, particularly human serum albumin, the present disclosure describes various alternative chemistries or configurations for the mass transport limiting membrane in lactate-responsive analyte sensors that may boost the lactate response sensitivity and the response stability to more desirable levels.

Some glucose-responsive analyte sensors may employ a crosslinked polyvinylpyridine-co-styrene polymer as a mass transport limiting membrane, in which a portion of the pyridine nitrogen atoms are functionalized with a non-crosslinked poly(ethylene glycol) side chain and a portion of the pyridine nitrogen atoms are functionalized with an alkylsulfonic acid group. Crosslinking of these membrane polymers in an analyte sensor may take place through functionalization with a bis-epoxide, such as polyethylene glycol diglycidyl ether (PEGDGE) or glycerol triglycidyl ether (Gly3). Such membrane polymers are, by themselves, ineffective for providing a stable response when analyzing for lactate. The present disclosure shows that these membrane polymers may be replaced with a polyethylene glycol-crosslinked polyvinylpyridine homopolymer or polyvinylpyridine copolymer (different from polyvinylpyridine-co-styrene) to afford improved lactate sensing performance, particularly in the form of extended response stability, when a serum albumin is co-present with lactate oxidase in the active area. Alternately and surprisingly, a polyethylene glycol-crosslinked polyvinylpyridine homopolymer or polyvinylpyridine copolymer may be suitably combined (either in a bilayer membrane or as a homogeneous admixture) with the crosslinked polyvinylpyridine-co-styrene polymer that is more commonly used for glucose analyses to afford satisfactory sensor performance when analyzing for lactate.

As defined herein, a "homopolymer" is a polymer containing only a single type of monomer unit defining the polymer backbone. In a crosslinked homopolymer, some of the monomer units may bear a crosslinking group and some of the monomer units may not. Monomer units bearing or lacking a crosslinking group are considered to represent the same monomer unit, as defined herein. As defined, herein, a "copolymer" is a polymer containing two or more different types of monomer units defining the polymer backbone. The two or more different types of monomer units have different structures (including isomeric variations of the same structure). In a crosslinked copolymer, either type of monomer unit may bear a crosslinking agent, and some of the monomer units of either type may bear a crosslinking group and some may not.

Before describing the analyte sensors of the present disclosure in more detail, a brief overview of suitable in vivo analyte sensor configurations and sensor systems employing the analyte sensors will first be provided so that the embodiments of the present disclosure may be better understood.

FIG. 1 shows a diagram of an illustrative sensing system that may incorporate an analyte sensor of the present disclosure. As shown, sensing system 100 includes sensor control device 102 and reader device 120 that are configured to communicate with one another over a local communication path or link 14Q, which may be wired or wireless, uni- or bi-directional, and encrypted or non-encrypted. Reader device 120 may constitute an output medium for viewing analyte concentrations, such as a lactate concentration, and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately, sensor 104 may communicate directly with remote terminal 170 and/or trusted computer systems 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 an incorporated herein by reference in its entirety. Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's analyte levels. Reader device 120 may comprise display 122 and optional input component 121. Display 122 may comprise a touch-screen interface, according to some embodiments.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Sensor 104 may comprise a sensor tail of sufficient length for insertion to a desired depth in a given tissue. The sensor tail may comprise a working electrode and one or more active areas (sensing regions/spots or sensing layers) located upon the working electrode and that are active for sensing an analyte of interest, particularly lactate according to the present disclosure. According to one or more embodiments of the present disclosure, each active area may comprise a lactate-responsive enzyme, suitable examples of which may include lactate oxidase or lactate dehydrogenase. The active areas may include a polymeric material to which the enzyme is covalently bonded, according to some embodiments. In various embodiments of the present disclosure, lactate may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, the analyte sensors of the present disclosure may be adapted for assaying dermal fluid or interstitial fluid.

In some embodiments, sensor 104 may automatically forward data to reader device 120. For example, analyte concentration data may be communicated automatically and periodically, such as at a certain frequency as data is obtained or after a certain time period has passed, with the data being stored in a memory until transmittal (e.g., every minute, five minutes, or other predetermined time period). In other embodiments, sensor 104 may communicate with reader device 120 in a non-automatic manner and not according to a set schedule. For example, data may be communicated from sensor 104 using RFID technology when the sensor electronics are brought into communication range of reader device 120. Until communicated to reader device 120, data may remain stored in a memory of sensor 104. Thus, a patient does not have to maintain close proximity to reader device 120 at all times, and can instead upload data at a convenient time. In yet other embodiments, a combination of automatic and non-automatic data transfer may be implemented. For example, data transfer may continue on an automatic basis until reader device 120 is no longer in communication range of sensor 104.

An introducer may be present transiently to promote introduction of sensor 104 into a tissue. In illustrative embodiments, the introducer may comprise a needle or similar sharp. It is to be recognized that other types of introducers, such as sheaths or blades, may be present in alternative embodiments. More specifically, the needle or other introducer may transiently reside in proximity to sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 250 microns. It is to be recognized, however, that suitable needles may have a larger or smaller cross-sectional diameter if needed for particular applications.

In some embodiments, a tip of the needle (while present) may be angled over the terminus of sensor 104, such that the needle penetrates a tissue first and opens an access pathway for sensor 104. In other illustrative embodiments, sensor 104 may reside within a lumen or groove of the needle, with the needle similarly opening an access pathway for sensor 104. In either case, the needle is subsequently withdrawn after facilitating sensor insertion.

Suitable configurations for the analyte sensors of the present disclosure may employ two-electrode or three-electrode detection motifs, which are described further hereinafter in reference to FIGS. 2A-2C.

Three-electrode detection motifs may comprise a working electrode, a counter electrode, and a reference electrode. Related two-electrode detection motifs may comprise a working electrode and a second electrode, in which the second electrode functions as both a counter electrode and a reference electrode (i.e., a counter/reference electrode). In both two-electrode and three-electrode detection motifs, an active area of the analyte sensor may be in contact with the working electrode. The active area may comprise a lactate-responsive enzyme and a stabilizer, particularly a serum albumin, according to the embodiments of the present disclosure. In some embodiments, the various electrodes may be at least partially stacked (layered) upon one another, as described in further detail hereinafter. In some or other embodiments, the various electrodes may be laterally spaced apart from one another upon the sensor tail. In either case, the various electrodes may be electrically isolated from one another by a dielectric material or similar insulator.

Figure 2A:
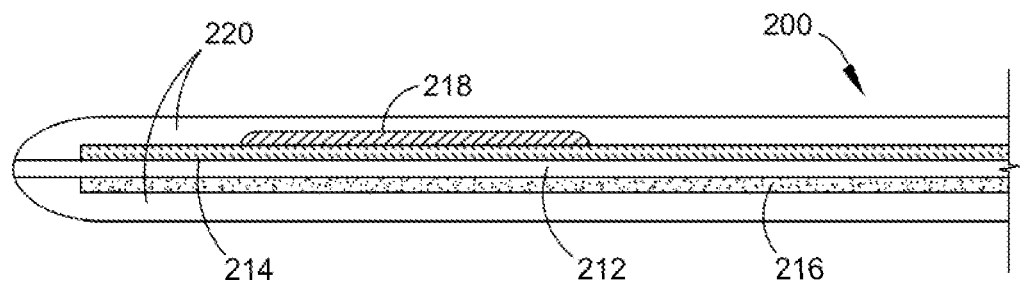
FIG. 2A shows a diagram of an illustrative two-electrode analyte sensor configuration, which is compatible for use in some embodiments of the disclosure herein.

FIG. 2A shows a diagram of an illustrative two-electrode analyte sensor configuration, which is compatible for use in some embodiments of the disclosure herein. As shown, analyte sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active area 218 is disposed as at least one layer upon at least a portion of working electrode 214. In various embodiments of the present disclosure, active area 218 may comprise multiple spots or a single spot configured for detection of lactate.

Referring still to FIG. 2A, membrane 220 overcoats at least active area 218 and may optionally overcoat some or all of working electrode 214 and/or counter/reference electrode 216, or the entirety of analyte sensor 200, according to some embodiments. One or both faces of analyte sensor 200 may be overcoated with membrane 220. Membrane 220 may comprise one or more polymeric membrane materials having capabilities of limiting analyte flux to active area 218 (i.e., membrane 220 is a mass transport limiting membrane). The composition of membrane 220 may vary to promote a desired flux of lactate to active area 218, thereby providing a desired signal intensity and stability as described further herein. Analyte sensor 200 may be operable for assaying for lactate by any of coulometric, amperometric, voltammetric, or potentiometric electrochemical detection techniques. Particular compositions for membrane 220 that may be suitable when analyzing for lactate are discussed further herein.

Figure 2B:
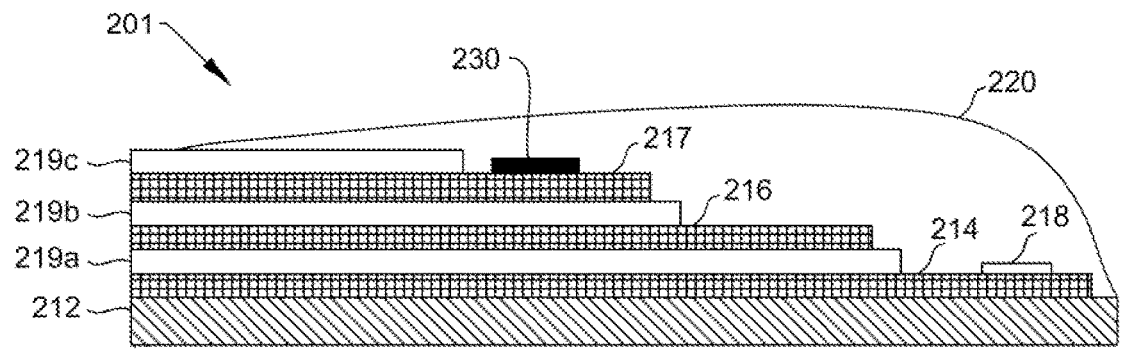
FIGS. 2B and 2C show diagrams of illustrative three-electrode analyte sensor configurations, which are compatible for use in some embodiments of the disclosure herein.
Figure 2C:
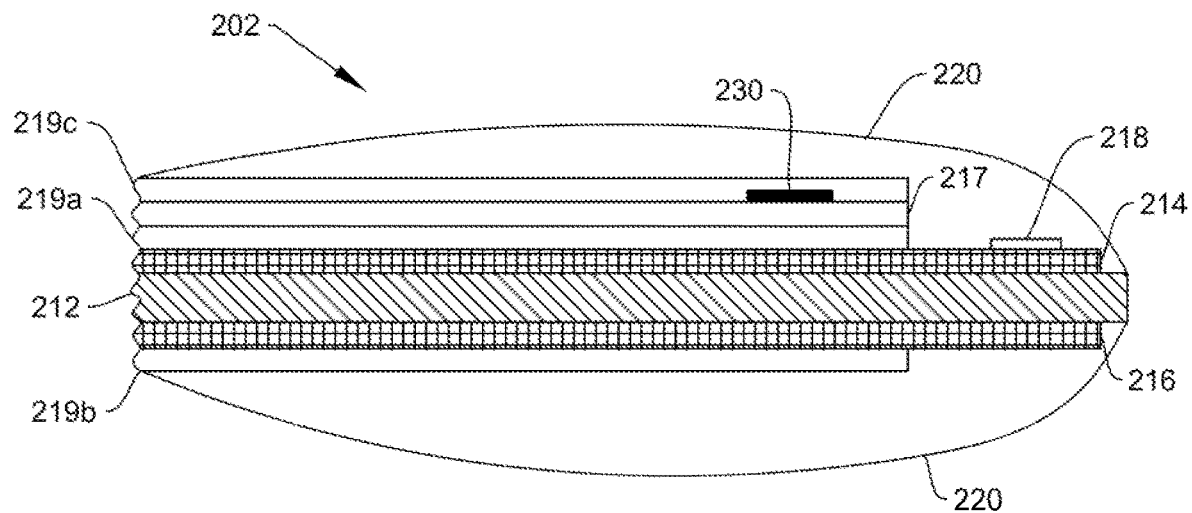

FIGS. 2B and 2C show diagrams of illustrative three-electrode analyte sensor configurations, which are also compatible for use in some embodiments of the disclosure herein. Three-electrode analyte sensor configurations may be similar to that shown for analyte sensor 200 in FIG. 2A, except for the inclusion of additional electrode 217 in analyte sensors 201 and 202 (FIGS. 2B and 2C). With additional electrode 217, counter/reference electrode 216 may then function as either a counter electrode or a reference electrode, and additional electrode 217 fulfills the other electrode function not otherwise accounted for. Working electrode 214 continues to fulfill its original function. Additional electrode 217 may be disposed upon either working electrode 214 or electrode 216, with a separating layer of dielectric material in between. For example, as depicted in FIG. 2B, dielectric layers 219a, 219b and 219c separate electrodes 214, 216 and 217 from one another and provide electrical isolation. Alternately, at least one of electrodes 214, 216 and 217 may be located upon opposite faces of substrate 212, as shown in FIG. 2C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Reference material layer 230 (e.g., Ag/AgCl) may be present upon electrode 217, with the location of reference material layer 230 not being limited to that depicted in FIGS. 2B and 2C. As with sensor 200 shown in FIG. 2A, active area 218 in analyte sensors 201 and 202 may comprise multiple spots or a single spot configured for detection of lactate. Additionally, analyte sensors 201 and 202 may be operable for assaying lactate by any of coulometric, amperometric, voltammetric, or potentiometric electrochemical detection techniques.

Like analyte sensor 200, membrane 220 may also overcoat active area 218, as well as other sensor components, in analyte sensors 201 and 202, thereby serving as a mass transport limiting membrane. Additional electrode 217 may be overcoated with membrane 220 in some embodiments. Although FIGS. 2B and 2C have depicted all of electrodes 214, 216 and 217 as being overcoated with membrane 220, it is to be recognized that only working electrode 214 may be overcoated in some embodiments. Moreover, the thickness of membrane 220 at each of electrodes 214, 216 and 217 may be the same or different. As in two-electrode analyte sensor configurations (FIG. 2A), one or both faces of analyte sensors 201 and 202 may be overcoated with membrane 220 in the sensor configurations of FIGS. 2B and 2C, or the entirety of analyte sensors 201 and 202 may be overcoated. Accordingly, the three-electrode sensor configurations shown in FIGS. 2B and 2C should be understood as being non-limiting of the embodiments disclosed herein, with alternative electrode and/or layer configurations remaining within the scope of the present disclosure.

According to various embodiments of the present disclosure, an electron transfer agent may be present in the active area of any of the analyte sensors or analyte sensor configurations disclosed herein. Suitable electron transfer agents may facilitate conveyance of electrons to or from the working electrode when an analyte (enzyme substrate), such as lactate, undergoes an oxidation-reduction reaction. Particular embodiments of the analyte sensors disclosed herein may feature an active area comprising lactate oxidase and a serum albumin, particularly human serum albumin, in combination with a mass transport limiting membrane compatible with lactate, as described further hereinbelow.

Suitable electron transfer agents may include electroreducible and electrooxidizable ions, complexes or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605,200, which are incorporated herein by reference in their entirety. Additional examples include those described in U.S. Pat. Nos. 6,736,957, 7,501,053 and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), or cobalt, including metallocene compounds thereof, for example. Suitable examples of electron transfer mediators and polymer-bound electron transfer mediators may include those described in U.S. Pat. Nos. 8,444,834, 8,268,143 and 6,605,201, the disclosures of which are incorporated herein by reference in their entirety. Suitable ligands for the metal complexes may also include, for example, bidentate or higher denticity ligands such as, for example, bipyridine, biimidazole, phenanthroline, or pyridyl (imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere.

According to various embodiments of the present disclosure, a polymer may be present in each active area of the analyte sensors or analyte sensor configurations disclosed herein. Suitable polymers for inclusion in the active areas may include, but are not limited to, polyvinylpyridines (e.g., poly(4-vinylpyridine)), polyvinylimidazoles (e.g., poly(l-vinylimidazole)), any mixture thereof, or any copolymer thereof. Illustrative copolymers that may be suitable for inclusion in the active area include those containing monomer units such as styrene, acrylamide, methacrylamide, or acrylonitrile, for example. In illustrative embodiments, the polymer within the active area of the analyte sensors disclosed herein may be a poly(4-vinylpyridine), in which a portion of the monomer units are functionalized with an alkylcarboxylate side chain, a portion of the monomer units are appended to the electron transfer agent with an amido spacer group (see Formula 1 below, for example), and a portion of the monomer units are unfunctionalized.

According to various embodiments of the present disclosure, the electron transfer agent may be covalently bonded to the polymer in the active area. The manner of covalent bonding is not considered to be particularly limited. Covalent bonding of the electron transfer agent to the polymer may take place by polymerizing a monomer unit bearing a covalently bound electron transfer agent, or the electron transfer agent may be reacted with the polymer separately after the polymer has already been synthesized. According to some embodiments, a bifunctional spacer may covalently bond the electron transfer agent to the polymer within the active area, with a first functional group being reactive with the polymer (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

Similarly, according to some or other various embodiments of the present disclosure, the enzyme within the active area may be covalently bonded to the polymer. According to more specific embodiments, covalent bonding of the enzyme to the polymer may take place via a crosslinker introduced with a suitable crosslinking agent. Suitable crosslinking agents for reaction with free amino groups in the enzyme (e.g., with the free amine in lysine) may include crosslinking agents such as, for example, polyethylene glycol diglycidylether (PEGDGE) or other polyepoxides (e.g., Gly3), cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking is generally intermolecular, but can be intramolecular in some embodiments.

The electron transfer agent and/or the enzyme may be associated with the polymer in the active area through means other than covalent bonding as well. In some embodiments, the electron transfer agent and/or the enzyme may be ionically or coordinatively associated with the polymer. For example, a charged polymer may be ionically associated with an oppositely charged electron transfer agent or enzyme. In still other embodiments, the electron transfer agent and/or the enzyme may be physically entrained within the polymer without being bonded thereto.

Various configurations for lactate-responsive analyte sensors of the present disclosure will now be described in further detail. According to various embodiments, analyte sensors of the present disclosure may comprise: a working electrode having an active area disposed thereon, and a mass transport limiting membrane overcoating at least the active area upon the working electrode. The active area comprises a polymer, an albumin, and a lactate-responsive enzyme covalently bonded to the polymer. In more specific embodiments, the mass transport limiting membrane may comprise at least a crosslinked polyvinylpyridine homopolymer or copolymer. The mass transport limiting membrane may be single-component or multi-component. Multi-component membrane embodiments may comprise a bilayer or homogeneous admixture of the crosslinked polyvinylpyridine and another polymer, according to more particular embodiments of the present disclosure.

Suitable polyvinylpyridine copolymers for inclusion in the mass transport limiting membrane may comprise up to about 25% comonomers (based on the total amount of monomers in the copolymer), such as from about 0.1% to about 5% comonomers, or about 5% to about 15% comonomers, or about 15% to about 25% comonomers, or about 1% to about 10% co-monomers. Suitable comonomers are not particularly limited, provided that the mass transport limiting membrane affords sufficient lactate permeability to provide an analyte sensitivity of about 1 nA/mM or greater when exposed to lactate. The polyvinylpyridine copolymer may be distinct from a polyvinylpyridine-co-styrene copolymer, according to various embodiments.

The foregoing analyte sensors may further comprise a counter electrode and a reference electrode, or a counter/reference electrode. Suitable configurations for the analyte sensors are described in greater detail hereinabove in reference to FIGS. 2, 3A and 3B. Other configurations for the various electrodes and active areas also reside within the spirit and scope of the present disclosure, and the depicted sensor configurations should not be considered as limiting of the scope of the present disclosure.

Analyte sensors of the present disclosure may alternately comprise: a working electrode having an active area disposed thereon, and a mass transport limiting membrane overcoating at least the active area upon the working electrode, in which the active area comprises a polymer, an albumin, and a lactate-responsive enzyme covalently bonded to the polymer, and the mass transport limiting membrane comprises a membrane polymer that is permeable to lactate. More specifically, the mass transport limiting membrane may have a lactate permeability such that the sensitivity of the analyte sensor is at least about 5 nA at a lactate concentration of about 5 mM. That is, the analyte sensitivity of the analyte sensors is about 1 nA/mM or greater when exposed to lactate. The membrane polymer may comprise a polyethyleneglycol-crosslinked polyvinylpyridine homopolymer or copolymer in more specific embodiments, either as a single-component membrane or a multi-component membrane, such as a bilayer of homogeneous admixture.

Still other analyte sensors of the present disclosure may alternately comprise: a working electrode having an active area disposed thereon, and a mass transport limiting membrane overcoating at least the active area upon the working electrode, in which the active area comprises a polymer, a catalase, and a lactate-responsive enzyme covalently bonded to the polymer, and the mass transport limiting membrane comprises at least a crosslinked polyvinylpyridine homopolymer or copolymer.

According to various embodiments, the lactate-responsive enzyme within the active area may comprise lactate oxidase or lactate dehydrogenase. In more specific embodiments, the combination of lactate oxidase and albumin, particularly human serum albumin, may be advantageous for conducting lactate analyses according to the present disclosure.

According to more specific embodiments, lactate oxidase may be present in the active area in an amount ranging from about 0.05 µg to about 5 µg, or from about 0.1 µg to about 4 µg, or from about 0.2 µg to about 3 µg, or from about 0.5 µg to about 2 µg. In terms of weight percentage of the active area, the lactate oxidase may be present in an amount ranging from about 10% to about 90% by weight of the active area, or from about 25% to about 75% by weight of the active area, or from about 30% to about 60% by weight of the active area.

According to various embodiments, the albumin within the active area may comprise human serum albumin. Alternately, non-human albumin may be satisfactorily used, such as bovine serum albumin.

The albumin may be incorporated within the active area in an amount sufficient to stabilize the lactate-responsive enzyme, particularly lactate oxidase, according to the disclosure herein. In more specific embodiments, the albumin may be present in the active area in an amount ranging from about 0.05 µg to about 5 µg, or from about 0.1 µg to about 2 µg, or from about 0.2 µg to about 1.5 µg, or from about 0.3 µg to about 0.8 µg. In terms of weight percentage of the active area, the albumin may be present in an amount ranging from about 25% to about 75% by weight of the active area, or from about 30% to about 60% by weight of the active area. In certain embodiments, the weight ratio of lactate oxidase to albumin may range from about 10:1 to about 1:10 (w/w), or from about or from about 5:1 to about 1:5, or from about 5:1 to about 1:1, or from about 2:1 to about 1:1, or from about 1:1 to about 1:5, or from about 1:1 to about 1:2.

In more specific embodiments, the analyte sensors of the present disclosure may comprise a sensor tail configured for insertion into a tissue. The working electrode is disposed upon the sensor tail and may be inserted in the tissue to facilitate lactate analyses therein. Suitable tissues are not considered to be particularly limited and specific examples are addressed in more detail above. Similarly, considerations for deploying a sensor tail at a particular position or depth within a tissue are addressed above.

The particular configuration of the analyte sensors disclosed herein, including the amounts of albumin and lactate oxidase to incorporate in the active area, may depend upon the tissue penetrated by the sensor tail, the anticipated concentrations of lactate to be analyzed, and the specific conditions under which the analyte sensors are intended to operate while analyzing lactate. In more specific embodiments, the tissue penetrated by the analyte sensors may be skin, such that the sensor tail is positioned within a dermal layer, an interstitial layer, or a subcutaneous layer below the surface of the skin. The sensor may further be contained within a sensor housing that is configured for adherence to the skin.

As mentioned above, the active area of the analyte sensors may comprise an electron transfer agent that is covalently bonded to the polymer therein. The manner of covalent bonding between the polymer and the electron transfer agent is not considered to be particularly limited. Suitable types of covalent bonding between the polymer and the electron transfer agent are described in further detail hereinabove.

Ideally, the active area may be configured to attain a steady state current rapidly upon operating the analyte sensors of the present disclosure at a given potential. Rapid attainment of a steady state current may be promoted by choosing an electron transfer agent that changes its oxidation state quickly upon being exposed to a potential at or above its oxidation-reduction potential. Making the active areas as thin as possible may also facilitate rapid attainment of a steady state current. For example, suitable thicknesses for the active area may range from about 0.1 microns to about 10 microns. In some or other embodiments, combining a conductive material such as, for example, carbon nanotubes, graphene, or metal nanoparticles within the active area may promote rapid attainment of a steady state current. Suitable amounts of conductive particles may range from about 0.1% to about 50% by weight of the active area, or from about 1% to about 50% by weight, or from about 0.1% to about 10% by weight, or from about 1% to about 10% by weight.

The active area upon the working electrode of the analyte sensors disclosed herein may comprise at least one spot or layer disposed upon the working electrode. Each spot or layer may range in size from about 0.01 mm$^2$ to about 1 mm$^2$, although larger or smaller active area spots or layers are also contemplated herein. The total size of the active area (combined area of all spots or layers) may be up to about 100 mm$^2$, particularly about 25 mm$^2$ or less, or about 10 mm$^2$ or less, or about 5 mm$^2$ or less, or about 1 mm$^2$ or less, or about 0.1 mm$^2$ or less. In more particular embodiments, the total size of the active area may range from about 0.05 mm$^2$ to about 0.1 mm$^2$. Although the active area may comprise one spot or layer in some embodiments, more typical embodiments of the analyte sensors of the present disclosure feature an active area having a plurality of spots disposed upon the working electrode. The number of spots is not considered to be particularly limited, but may range from 2 to about 10, or from about 3 to about 8, or from about 4 to about 6, according to some embodiments.

It is also to be further appreciated that the sensitivity (output current) of the analyte sensors toward lactate may be varied by changing the coverage (area or size) of the active area, the identity and thickness of the mass transport limiting membrane overcoating the active area, and any combination thereof. Variation of these parameters to achieve a desired sensitivity may be conducted readily by one having ordinary skill in the art once granted the benefit of the disclosure herein.

The analyte sensors disclosed herein, particularly those having an active area comprising an albumin and covalently bound lactate oxidase and a mass transport limiting membrane comprising a polyvinylpyridine homopolymer or copolymer, particularly a polyvinylpyridine homopolymer, may be characterized functionally as having a response stability (change in output current) that varies by about 10% or less over 190 hours of measurement, or by about 5% or less over 190 hours of measurement, or by about 1% or less over 190 hours of measurement. Whatever variance does occur over this timeframe is expected to be clinically insignificant (i.e., have a marginal impact on the Clark error grid analysis and/or MARD or MAD analyses). Thus, it is to be anticipated that the catalase-stabilized lactate-responsive analyte sensors described in the foregoing patent would display still lower response currents at 190 hours of measurement.

In order to realize sufficient response stability, the analyte sensors of the present disclosure employ a mass transport limiting membrane that is selected for compatibility with lactate. More particularly, advantageous mass transport limiting membranes suitable for use in conjunction with a lactate-responsive enzyme, particularly lactate oxidase, may comprise a crosslinked polyvinylpyridine homopolymer or copolymer. The mass transport limiting membrane in the analyte sensors of the present disclosure may comprise only a single polymer (i.e., the crosslinked polyvinylpyridine homopolymer or copolymer), or it may be multi-component and comprise two or more polymers (i.e., the crosslinked polyvinylpyridine homopolymer or copolymer and at least a second crosslinked polymer in either a bilayer or homogenous admixture configuration). More specifically, the multi-component membrane may comprise a first polymer comprising a crosslinked polyvinylpyridine homopolymer and a second polymer comprising a crosslinked polyvinylpyridine copolymer, or a first polymer comprising a first crosslinked polyvinylpyridine copolymer and a second polymer comprising a second crosslinked polyvinylpyridine copolymer that differs from the first crosslinked polyvinylpyridine copolymer. In more specific embodiments, the second crosslinked polymer may comprise a crosslinked polyvinylpyridine copolymer, particularly a crosslinked polyvinylpyridine-co-styrene polymer in which a portion of the pyridine nitrogen atoms are functionalized with a non-crosslinked poly(ethylene glycol) tail and a portion of the pyridine nitrogen atoms are functionalized with an alkylsulfonic acid group.

Multi-component membranes suitable for use in conjunction with a lactate-responsive enzyme, particularly lactate oxidase, in the analyte sensors of the present disclosure may comprise a bilayer membrane, according to various embodiments. Suitable bilayer membranes may comprise a first layer comprising the crosslinked polyvinylpyridine homopolymer or copolymer and a second layer comprising the second crosslinked polymer, particularly a crosslinked polyvinylpyridine copolymer. The second layer may comprise a polyvinylpyridine copolymer different from a polyvinylpyridine copolymer in the first layer. In more particular embodiments, the first layer may be disposed directly upon the active area, and the second layer may be disposed upon the first layer. In alternative embodiments, the second layer may be disposed directly upon the active area, and the first layer may be disposed upon the second layer. The thicknesses and ordering of the first layer and the second layer may be varied in order to afford a desired sensitivity. Such bilayer configurations may be prepared, in some embodiments, by coating the first layer upon the active area (e.g., by spray coating, painting, inkjet printing, roller coating, dip coating, or the like) and then coating the second layer upon the first layer by the same or different coating technique (e.g., by spray coating, painting, inkjet printing, roller coating, dip coating, or the like). In other embodiments, the bilayer membrane may be configured with the first layer and the second layer reversed (thereby reversing the location of the crosslinked polyvinylpyridine homopolymer or copolymer), with each layer being coated as above.

Bilayer membranes, by their very nature, are heterogeneous, since two different membrane polymers are layered upon one another. Other multi-component membranes suitable for use in conjunction with a lactate-responsive enzyme, particularly lactate oxidase, in the analyte sensors of the present disclosure may be homogeneous in composition. More specifically, in some embodiments, suitable multi-component membranes may comprise a homogeneous admixture of the crosslinked polyvinylpyridine homopolymer or copolymer and the crosslinked second polymer, particularly a crosslinked polyvinylpyridine copolymer. The two crosslinked polyvinylpyridine copolymers may be different from one another. The ratio of the two crosslinked crosslinked polymers in the homogeneous admixture may vary over a considerable range, and the ratio may be adjusted to afford a desired sensitivity of the analyte sensors disclosed herein.

Figure 14:
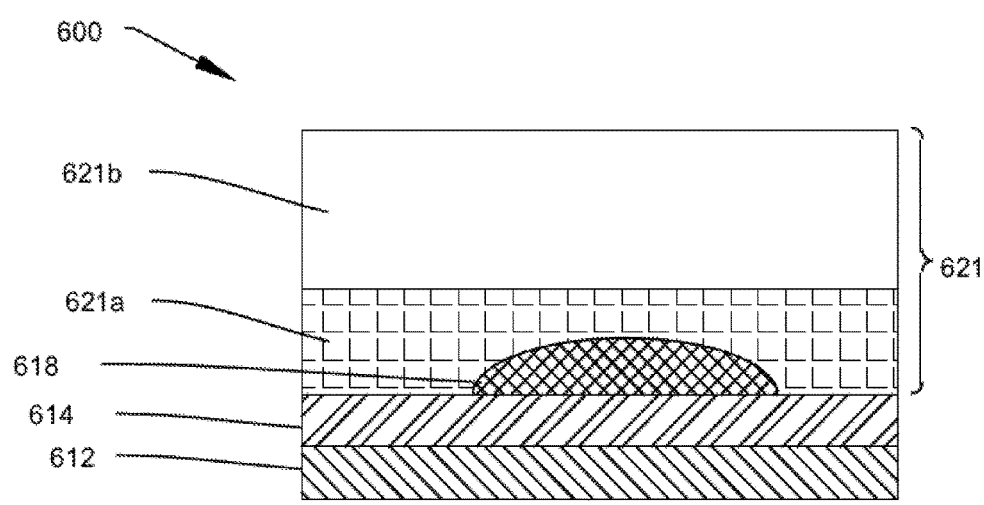
FIG. 14 shows an illustrative schematic of a portion of an analyte sensor having a bilayer membrane disposed upon a working electrode, which is compatible for use in some embodiments of the disclosure herein.

FIG. 14 shows an illustrative schematic of a portion of an analyte sensor having a bilayer membrane disposed upon a working electrode, which is compatible for use in some embodiments of the disclosure herein. As shown in FIG. 14, the analyte sensor features sensor tail 600 having working electrode 614 disposed on substrate 612. Active area 618 is disposed upon working electrode 614 and contains a lactate-responsive enzyme, in accordance with the disclosure herein.

As further shown in FIG. 14, active area 618 is overcoated with bilayer membrane 621, which comprises membrane layer 621a in direct contact with active area 618 and membrane layer 621b overlaying membrane layer 621a. Membrane layers 621a and 621b may comprise different membrane polymers, at least one of which is a polyvinylpyridine homopolymer or copolymer, according to the disclosure herein.

In alternative embodiments, a homogenous membrane layer comprising an admixture of the different membrane polymers may replace bilayer membrane 621 of FIG. 14 according to the disclosure herein.

The analyte sensors described hereinabove may be utilized in various methods for assaying lactate and determining a concentration of lactate therefrom. The concentration of lactate may be further correlated to a physiological condition (e.g., resulting from disease or exposure to environmental factors), according to various embodiments, as described in additional detail hereinbelow.

According to various embodiments, methods of the present disclosure may comprise, exposing an analyte sensor to a fluid, in which the analyte sensor comprises a working electrode having an active area disposed thereon and a mass transport limiting membrane overcoating at least the active area upon the working electrode. The active area comprises a polymer, an albumin, and a lactate-responsive enzyme, particularly lactate oxidase, that is covalently bonded to the polymer. The mass transport limiting membrane may comprise at least a crosslinked polyvinylpyridine homopolymer or copolymer in particular embodiments. The methods additionally comprise obtaining a signal at or above an oxidation-reduction potential of the active area, in which the signal is proportional to a concentration of lactate in the fluid, and correlating the signal to the concentration of lactate in the fluid.

In more specific embodiments, the fluid is a biological fluid and the analyte sensor is exposed to the biological fluid in vivo within a subject in whom measurement of a concentration of lactate is desired. The subject can be a human, according to still more specific embodiments of the present disclosure. Suitable biological fluids for analysis with the analyte sensors of the present disclosure may include any of the biological fluids discussed in more detail hereinabove.

The signal associated with the active area upon exposure to lactate may be correlated to a corresponding lactate concentration by consulting a lookup table or a calibration curve. The lookup table or calibration curve may be present in physical form (i.e., written form) or electronic form (i.e., a database or computer algorithm). A lookup table for various concentrations of lactate may be populated by assaying multiple samples having known lactate concentrations and recording the analyte sensor response at each concentration. Similarly, a calibration curve for lactate may be determined by plotting the analyte sensor response for each lactate sample as a function of the concentration. According to some embodiments, the calibration curve for analyte sensors of the present disclosure may be linear or near-linear with respect to the concentration of lactate. A background response may be subtracted from the analyte sensor response, in some embodiments, before the analyte sensor response is recorded or plotted. The background response may be determined by assaying a fluid lacking lactate (i.e., a blank). The lookup table or calibration curve may be consulted manually or electronically to determine the concentration of lactate in the fluid, as described further hereinafter.

A processor may determine which sensor response value in a lookup table is closest to that measured for a sample (fluid) having an unknown lactate concentration and then report the lactate concentration accordingly. In some or other embodiments, if the sensor response value for a sample having an unknown lactate concentration is between the recorded values in the lookup table, the processor may interpolate between two lookup table values to estimate the lactate concentration. Interpolation may assume a linear concentration variation between the two values reported in the lookup table. Interpolation may be employed, for example, when the sensor response for the sample differs by a sufficient amount from a given value in the lookup table, such as variation of about 10% or greater. Interpolation may similarly be performed when manually consulting a lookup table.

Likewise, a processor may input the sensor response value for a sample having an unknown lactate concentration into a corresponding calibration curve. The processor may then report the concentration of lactate accordingly.

The concentration of lactate determined using the analyte sensors of the present disclosure, as described above, may be further correlated to one or more physiological conditions. The one or more physiological conditions may be mediated by lactate in vivo and/or produce elevated or depressed lactate levels in vivo. More specifically, the one or more physiological conditions that may be monitored by the analyte sensors of the present disclosure include, for example, sepsis, infection, organ function, or any combination thereof. Other conditions in which monitoring of lactate may be beneficial include, for example, physiological stress and exercise, both of which may produce elevated lactate levels. Monitoring of any of these conditions may involve, for example, following lactate level trends over time and/or determining an instantaneous lactate level at a particular time. Optionally, an alert may be provided if the lactate level exceeds a defined threshold concentration for a given condition or if the lactate level is trending toward a defined threshold when monitored over time. As such, the analyte sensors disclosed herein may be configured to provide an alert or otherwise provide an indication that sepsis, infection, organ failure, or any combination thereof may be present. Depending upon the physiological condition(s) being monitored, the threshold concentration may vary.

Sepsis can be viewed as a three-stage syndrome, starting with sepsis and progressing through severe sepsis to septic shock. The goal is to treat sepsis during its early stage, before it becomes more dangerous. Currently, severe sepsis is often diagnosed by body temperature, heart rate, respiratory rate, decreased urine output, abrupt changes in mental status, and decreased platelet count. Septic shock is often diagnosed by the same markers in combination with an extremely low blood pressure.

Lactate levels may be useful to diagnose, monitor, and/or assess sepsis in its various forms and/or related infections. As such, determining a concentration of lactate according to the present disclosure may allow sepsis and/or infections to be more effectively monitored, assessed, and/or managed. Alternately, the analyte sensors of the present disclosure may be utilized to monitor a subject at risk for sepsis and/or infection but who is not presently exhibiting signs of either condition (e.g., a patient in a hospital). Lactate levels obtained according to the present disclosure may be diagnostically combined with other analyte levels and/or physiological markers (e.g., body temperature, heart rate, respiratory rate, blood pressure, decreased urine output, abrupt changes in mental status, decreased platelet count, and other markers (e.g., C reactive proteins (CRP), procalcitonin, pancreatic stone protein (PSP), circulating complement (C3 and C4), ferritin, cholesterol, albumin, cortisol, and neutrophil gelatinase associated lipocalin)) to diagnose and/or monitor the progression of sepsis and related infections in a subject. In particular embodiments, the concentration of lactate may be measured in cerebrospinal fluid to monitor, assess, and/or diagnose meningitis and/or septic meningitis. Additional markers for septic meningitis may include those such as, for example, glucose, sTREM-1, procalcitonin, CRP, TNF-$\alpha$, IL-1 $\beta$, IL-6, IL-8, and lipopolysaccharide binding protein. Additional markers for bacterial sepsis or bacterial infections may include, for example, glutamic acid, malate, pseudouridine, acetylcarnitine, glycerophosphocholine, hydroxyphenyllactic acid, acetylneuraminic acid, pseudouridine, and tyrosine. Additional markers for viral sepsis, including septic meningitis, or viral infections may include, for example, hypoxanthine, inosine and hexanoylcarnitine.

In some embodiments, the analyte sensors of the present disclosure may be used to monitor a subject's exposure to an infectious agent. For example, the analyte sensors may monitor the condition of the subject after acute exposure to an infectious agent to monitor for signs of sepsis or infection and/or to monitor the development and progression of the sepsis or infection. The analyte sensors may further be used to monitor the subject's response to anti-infective agents and/or treatments administered to the subject to treat the sepsis or infection or symptoms thereof.

Enzyme activity may also be diagnostic of organ function, in which the activity of the enzyme may be either hypoactive or hyperactive depending upon the particular organ and a given physiological condition being experienced by a subject. Within the realm of lactate-responsive enzymes, liver function and liver function physiological conditions (i.e., diseases) may be characterized in terms of the activity of lactate dehydrogenase. Other enzymes that may be desirable for organ function monitoring (including organs and organ functions differing from the liver and liver function), either alone or in combination with lactate dehydrogenase include, for example, creatine kinase, aspartate transaminase, aspartate aminotransferase, alkaline phosphatase, and 5' nucleotidase. Alternative organs, in addition to the liver, whose organ function may be monitored include, for example, the kidneys, heart, brain, lungs, pancreas, spleen, stomach, bladder, bones, gall bladder, intestines (large and small), colon, lymph nodes, and thyroid.

The analyte sensors disclosed herein may monitor organ function, particularly liver function, by assessing the activity of lactate dehydrogenase or another suitable lactate-responsive enzyme (e.g., lactate oxidase). The analyte sensors may be used to monitor, diagnose, and/or detect analyte levels in a subject experiencing dysregulated organ function or at risk of dysregulated organ function, possibly allowing organ disease to be identified prior to the development of life-threatening symptoms. The lactate concentration or the rate of change of lactate concentration determined by the analyte sensors disclosed herein may facilitate a diagnosis or analysis of organ failure or dysregulation or the possibility of organ failure or dysregulation. The analyte sensors may provide an alarm when lactate concentrations exceed threshold amount or are trending to exceed a threshold amount that may be characteristic of organ damage or failure.

Lactate levels obtained according to the present disclosure may be diagnostically combined with other analyte levels and/or physiological markers for determining organ function and/or failure, particularly of the liver. Additional markers that may be assayed in combination with lactate for assaying organ function include, for example, body temperature, heart rate, respiratory rate, blood pressure, decreased urine output, abrupt changes in mental status, decreased platelet count, and other markers (e.g., C reactive proteins (CRP), procalcitonin, pancreatic stone protein (PSP), circulating complement (C3 and C4), ferritin, cholesterol, albumin, cortisol, and neutrophil gelatinase associated lipocalin). The lactate levels monitored according to the present disclosure may be further utilized to reduce the time prior to beginning a course of therapy for combating organ failure and/or to monitor the progress of a course of therapy or treatment.

Embodiments disclosed herein include:

A. Analyte sensors. The analyte sensors comprise: a working electrode having an active area disposed thereon, the active area comprising a polymer, an albumin, and a lactate-responsive enzyme covalently bonded to the polymer; and a mass transport limiting membrane overcoating at least the active area upon the working electrode.

B. Methods for assaying lactate. The methods comprise: exposing an analyte sensor to a fluid; wherein the analyte sensor comprises: a working electrode having an active area disposed thereon, the active area comprising a polymer, an albumin, and a lactate-responsive enzyme covalently bonded to the polymer; and a mass transport limiting membrane overcoating at least the active area upon the working electrode; obtaining a signal at or above an oxidation-reduction potential of the active area, the signal being proportional to a concentration of lactate in the fluid; and correlating the signal to the concentration of lactate in the fluid.

C. Lactate sensors responsive to sepsis, infection, or organ function. The lactate sensors comprise: An analyte sensor comprising: a working electrode having an active area disposed thereon, the active area comprising a polymer, an albumin, and a lactate-responsive enzyme covalently bonded to the polymer; and a mass transport limiting membrane overcoating at least the active area upon the working electrode; wherein the analyte sensor is responsive to sepsis, infection, organ function, or any combination thereof and is configured to provide an alert or other indication that sepsis, infection, organ failure, or any combination thereof may be present for a measured lactate concentration.

Each of embodiments A-C may have one or more of the following additional elements in any combination:

Element 1: wherein the albumin comprises human serum albumin.

Element 2: wherein the lactate-responsive enzyme comprises lactate oxidase.

Element 3: wherein the active area comprises a plurality of sensing spots disposed upon the working electrode.

Element 4: wherein the mass transport limiting membrane comprises a multi-component membrane, the multi-component membrane comprising the crosslinked polyvinylpyridine homopolymer or copolymer and at least a second crosslinked polymer.

Element 5: wherein the multi-component membrane comprises a first polymer comprising a crosslinked polyvinylpyridine homopolymer and second polymer comprising a crosslinked polyvinylpyridine copolymer, or a first polymer comprising a first crosslinked polyvinylpyridine copolymer and a second polymer comprising a second crosslinked polyvinylpyridine copolymer.

Element 6: wherein the multi-component membrane comprises a bilayer membrane, the bilayer membrane comprising a first layer comprising the polyvinylpyridine homopolymer or copolymer and a second layer comprising the second crosslinked polymer.

Element 7: wherein the first layer is disposed directly upon the active area and the second layer is disposed upon the first layer.

Element 8: wherein the mass transport limiting membrane comprises a homogeneous admixture of the crosslinked polyvinylpyridine homopolymer or copolymer and the second crosslinked polymer.

Element 9: wherein the working electrode is disposed upon a sensor tail that is configured for insertion into a tissue.

Element 10: wherein the active area further comprises an electron transfer agent that is covalently bonded to the polymer.

Element 11: wherein the fluid is a biological fluid and the analyte sensor is exposed to the biological fluid in vivo.

Element 12: wherein the method further comprises: determining a presence of one or more conditions in a subject based upon the concentration of lactate in the fluid, the one or more conditions being selected from the group consisting of sepsis, infection, organ function, and any combination thereof.

Element 13: The analyte sensor of claim 1, wherein the mass transport limiting membrane comprises at least a crosslinked polyvinylpyridine homopolymer or copolymer.

By way of non-limiting example, exemplary combinations applicable to A-CB include:

The analyte sensors of A or C or the method of B in combination with elements 1 and 2; 1, 2 and 13; 1 and 3; 1, 3 and 13; 1-3; 1-3 and 13; 1 and 4; 1, 4 and 13; 1 and 13; 2 and 4; 2, 4 and 13; 2 and 13; 3 and 4; 3, 4 and 13; 3 and 13; 1-4; 1-4 and 13; 2-4; 2-4 and 13; 1, 4 and 5; 1, 4, 5 and 13; 2, 4 and 5; 2, 4, 5 and 13; 3-5; 3-5 and 13; 4 and 5; 4, 5 and 13; 1 and 4-6; 1, 4-6 and 13; 2, 4, 5 and 6; 2, 4, 5, 6 and 13; 3-6; 3-6 and 13; 4-7; 4-7 and 13; 4 and 8; 4, 8 and 13; 4, 5 and 8; 4, 5, 8 and 13; 1 and 9; 1, 9 and 13; 2 and 9; 2, 9 and 13; 3 and 9; 3, 9 and 13; 4 and 9; 4, 9 and 13; 1 and 10; 1, 10 and 13; 2 and 10; 2, 10 and 13; 3 and 10; 3, 10 and 13; 4 and 10; 4, 10 and 13; 9 and 10; 9, 10 and 13. The method of B in combination with elements 1 and 11; 1, 11 and 13; 1 and 13; 2 and 11; 2 and 13; 3 and 11; 3 and 13; 4 and 11; 4 and 13; 4, 5 and 11; 4, 5, 11 and 13; 4-6 and 11; 4, 6, 11 and 13; 4-7 and 11; 4-7, 11 and 13; 4, 8 and 11; 4, 8, 11 and 13; 9 and 11; 9, 11 and 13; 10 and 11; 10, 11 and 13; 11 and 12; 11-13; 1 and 12; 1, 12 and 13; 2 and 12; 2, 12 and 13; 3 and 12; 3, 12 and 13; 4 and 12; 4, 12 and 13; 4, 5 and 12; 4, 5, 12 and 13; 4-6 and 12; 4-6, 12 and 13; 4-7 and 12; 4-7, 12 and 13; 4, 8 and 12; 4, 8, 12 and 13; 9 and 12; 9, 12 and 13; 10 and 12; 10, 12 and 13; 1, 11 and 12; 1 and 11-13; 2, 11 and 12; 2 and 11-13; 3, 11 and 12; 3 and 11-13; 4, 11 and 12; 4 and 11-13; 4, 5, 11 and 12; 4, 5, and 11-13; 4-6, 11 and 12; 4-6 and 11-13; 4-7, 11 and 12; 4-7 and 11-13; 4, 8, 11 and 12; 4, 8 and 11-13; 9, 11 and 12; 9 and 11-13; 10-12; and 10-13.

To facilitate a better understanding of the embodiments described herein, the following examples of various representative embodiments are given. In no way should the following examples be read to limit, or to define, the scope of the invention.

EXAMPLES

Example 1: Comparison of Lactate Sensor Response

Two different lactate oxidase/polymer formulations for active area deposition and two different membrane polymer formulations for mass transport limiting membrane deposition were prepared to assay the performance of lactate-responsive sensors featuring various permutations of these formulations. Formulation details and the process used for preparing the analyte sensors are discussed further below. In general, the analyte sensors were prepared similarly to corresponding glucose-responsive analyte sensors, except substituting lactate oxidase for glucose oxidase (with or without albumin) and using a different membrane polymer in some cases.

Formulations for Active Area Deposition:

Lactate oxidase was combined with the polymer of Formula 1 in aqueous solution formulations as specified in Tables 1 and 2 below. Further details concerning the polymer are provided in commonly owned U.S. Pat. No. 6,605,200, which is incorporated by reference in its entirety. The subscripts for each monomer represent illustrative atomic ratios.

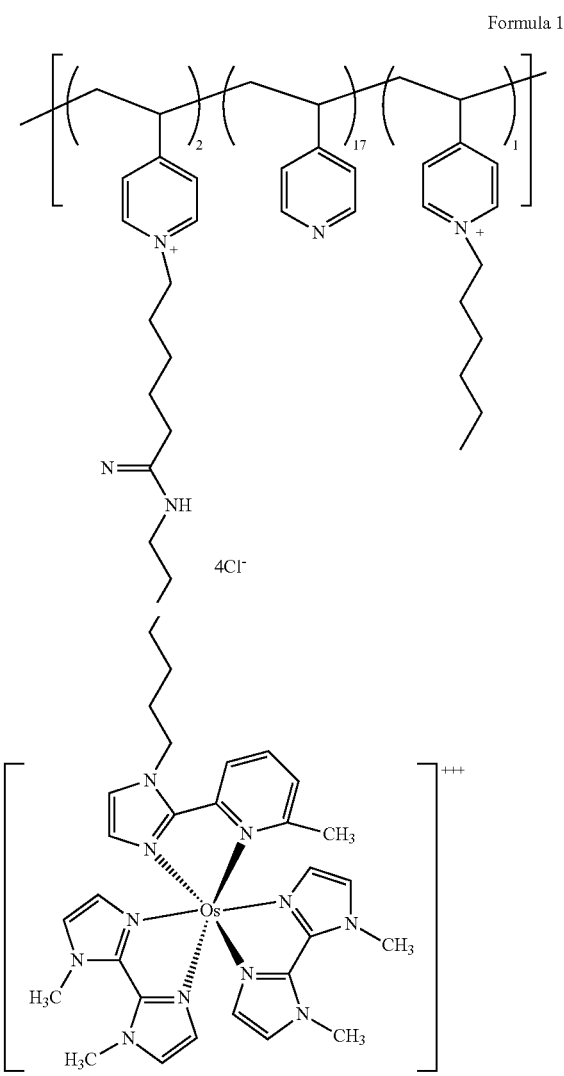

Formula 1

TABLE 1

Lactate Oxidase (LOX) in 10 mM HEPES Buffer at pH = 8
(Formulation 1)

| Component | Concentration (mg/mL) |
|---|---|
| LOX | 24.6 |
| Formula 1 Polymer | 20.4 |
| PEGDGE400 | 7.5 |

TABLE 2

Lactate Oxidase (LOX) in 10 mM MES Buffer at pH = 5.5
(Formulation 2)

| Component | Concentration (mg/mL) |
|---|---|
| LOX | 24.6 |
| Human Serum Albumin | 24.6 |
| Formula 1 Polymer | 9.2 |
| PEGDGE400 | 6.2 |

To deposit each active area, ~20 nL of each solution was deposited upon a carbon working electrode to form 6 discrete spots, each having an area of approximately 0.01 mm². Formulation 1 was dispensed 4 times and Formulation 2 was dispensed 6 times to form the spots. Following deposition, the working electrode was cured overnight at 25° C. Formulation 1 corresponds to that used for depositing the active area of glucose-responsive analyte sensors, except substituting lactate oxidase for glucose oxidase.

Formulations for Mass Transport Limiting Membrane Deposition:

Membrane polymer formulations were prepared in aqueous solution formulations specified in Tables 3 and 4 below.

TABLE 3

Polyvinylpyridine-co-Styrene Formulation in
80:20 Ethanol:HEPES Buffer-Gly3 Crosslinked
(Formulation 3)

| Component | Concentration (mg/mL) |
|---|---|
| Polyvinylpyridine-co-styrene polymer | 111.7 |
| Gly3 crosslinker | 7.0 |
| polydimethylsiloxane | 0.3 |

TABLE 4

Polyvinylpyridine Formulation in 80:20
Ethanol:HEPES Buffer-PEGDGE400 Crosslinked
(Formulation 4)

| Component | Concentration (mg/mL) |
|---|---|
| Polyvinylpyridine | 94.6 |
| PEGDGE400 crosslinker | 5.1 |
| polydimethylsiloxane | 0.3 |

Dip coating was used to deposit a mass transport limiting membrane upon each active area prepared as above. Formulation 3 was deposited using 4 dips, and Formulation 4 was deposited using 4 dips. A wait time of about 10 minutes between dips was used. Following the completion of dip coating, the membranes were cured for 24 hours at 25° C., followed by 48 hours at 56° C. in desiccated vials. Spray coating, screen printing, or similar processes may be alternately used to deposit the mass transport limiting membrane. Formulation 3 corresponds to that used for depositing a mass transport limiting membrane within glucose-responsive analyte sensors.

Lactate-responsive analyte sensors were prepared using the deposition conditions specified above. All possible combinations of active area and mass transport limiting membrane were prepared, with 8 sensors being fabricated for each possible combination. After fabrication, each sensor was exposed to a 5 mM lactate solution in 100 mM phosphate buffered saline (PBS) at 37° C. for 190 hours, with the working potential being held at +40 mV relative to Ag/AgCl. The tested combinations of active areas and mass transport limiting membranes are specified in Table 5. Testing results are shown in FIG. 3.

TABLE 5

| Sensor Group | Active Area | Mass Transport Limiting Membrane | Result |
|---|---|---|---|
| 1 | Formulation 1 | Formulation 3 | Poor sensitivity |
| 2 | Formulation 1 | Formulation 4 | Poor sensitivity |
| 3 | Formulation 2 | Formulation 3 | Variable sensitivity, decreasing signal intensity over time |
| 4 | Formulation 2 | Formulation 4 | High sensitivity, stable signal intensity over time |

Figure 3:
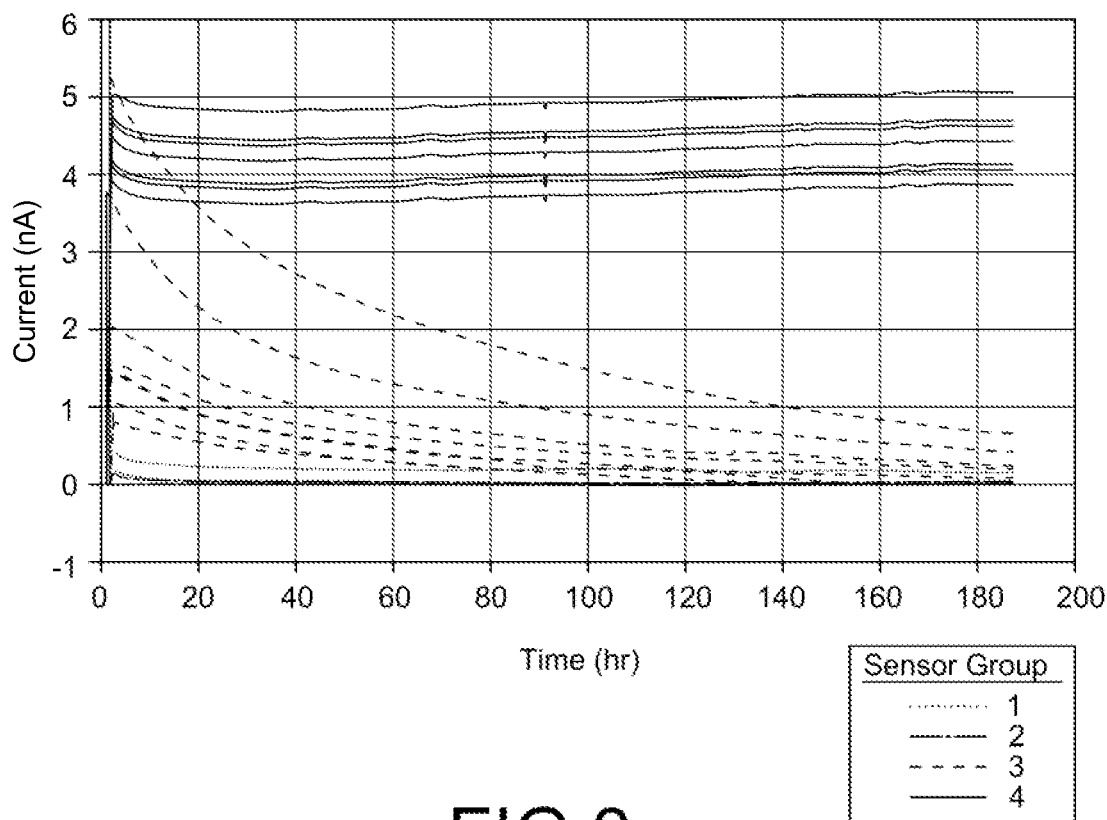
FIG. 3 shows an illustrative plot of sensor performance for Groups 1-4 in Example 1.

As shown in FIG. 3, lactate-responsive analyte sensors having active areas and mass transport limiting membranes formulated similarly to those used successfully in glucose-responsive analyte sensors (Group 1) afforded poor performance when exposed to lactate. As shown, the signal intensity was under 0.5 nA for all of the tested samples, which is undesirably low for a viable lactate-responsive sensor. The signal intensity was even poorer when polyvinylpyridine and a different crosslinking agent were substituted for the polyvinylpyridine-co-styrene and Gly3 crosslinker in Formulation 3 (Group 2).

Incorporation of human serum albumin considerably improved the sensor performance, as further shown in FIG. 3. Sample Group 3, for example, exhibited considerably higher signal intensities than were realized for any of the Group 1 or Group 2 samples. However, there was considerably variability in the initial signal intensity among this group of samples (>4 nA variance). Moreover, there was a steady decrease in the signal intensity from the initially observed maximum signal intensity. The response variability and the poor signal stability over time likewise makes the combination of this sample group unlikely to be suitable for a viable lactate-responsive analyte sensor.

Surprisingly, the combination of a human serum albumin-containing active area and a mass transport limiting membrane comprising crosslinked polyvinylpyridine homopolymer (Group 4) produced an acceptable combination of high signal intensity and extended signal stability over time. As shown in FIG. 3, all of the replicate sensors of Group 4 had initial signal intensities clustered within 1 nA of each other between 4 nA and 5 nA. This level of signal intensity and variability is within the range over which a commercially viable lactate-responsive analyte sensor might be developed. Moreover, the signal intensity only varied a few tenths of a nA or less over 190 hours of signal observation, which is again within a range that may be suitable for development of a commercially viable sensor.

Figure 4:
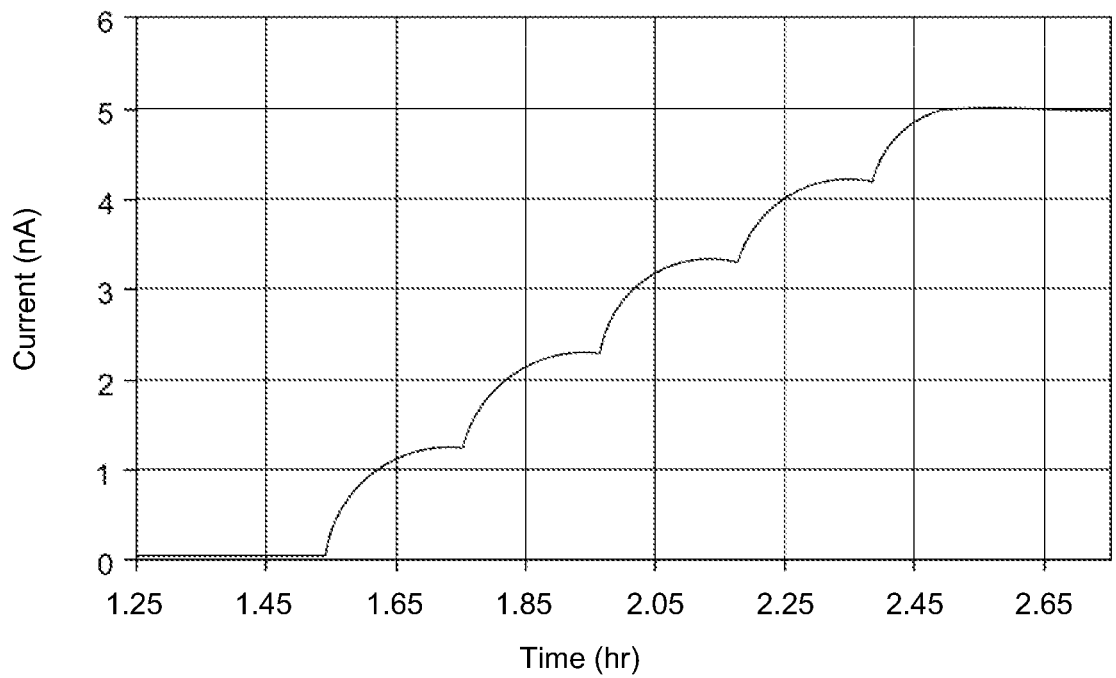
FIG. 4 shows an illustrative plot of the response of a Group 4 analyte sensor in Example 1 to lactate solutions having varying lactate concentrations.

As shown in FIG. 4, the observed current for the Group 4 sensors responded rapidly and achieved a stable value as increasing amounts of lactate were added in 1 mM increments to a PBS solution initially not containing lactate.

Example 2: Alternative Mass Transport Limiting Membranes

For these experiments, the lactate oxidase-containing active area was deposited from a solution formulated as specified in Table 2 above. Active area deposition on a carbon electrode and curing were performed as described in Example 1. The mass transport limiting membranes for various samples were formulated as specified below.

Unless otherwise indicated below, deposition of the mass transport limiting membrane upon the active area was performed by dip coating (1-5 dips of the electrode and a wait time of about 10 minutes between dips). Formulations for the mass transport limiting membrane are further specified below. Following the completion of dip coating, the membranes were cured for 24 hours at 25° C., followed by 48 hours at 56° C. in desiccated vials.

Sensor response was measured by placing the active area of the electrode in a beaker containing 100 mM pH=7.5 PBS at 37° C. The potential was raised to +40 mV versus Ag/AgCl, and the current was monitored continuously thereafter.

Alternative Crosslinker in Formulation 3 (Formulation 3').

Formulation 3 was modified with an alternative crosslinker as specified in Table 6 below. The modified formulation is designated as Formulation 3' herein.

TABLE 6

Polyvinylpyridine-co-styrene Formulation in 80:20 Ethanol:HEPES Buffer-PEGDGE400 Crosslinked (Formulation 3')

| Component | Concentration (mg/mL) |
|---|---|
| Polyvinylpyridine-co-styrene polymer | 132.9 |
| PEGDGE400 crosslinker | 4.8 |
| polydimethylsiloxane | 0.3 |

Formulation 3' was prepared by combining 4 mL of the membrane polymer in 80:20 ethanol:HEPES buffer (140 mg/mL), 0.2 mL of PEGDGE400 in 80:20 ethanol:HEPES buffer (100 mg/mL), and 0.0132 mL of aminopropyl-terminated polydimethylsiloxane (PDMS) in ethanol (100 mg/mL).

Figure 5:
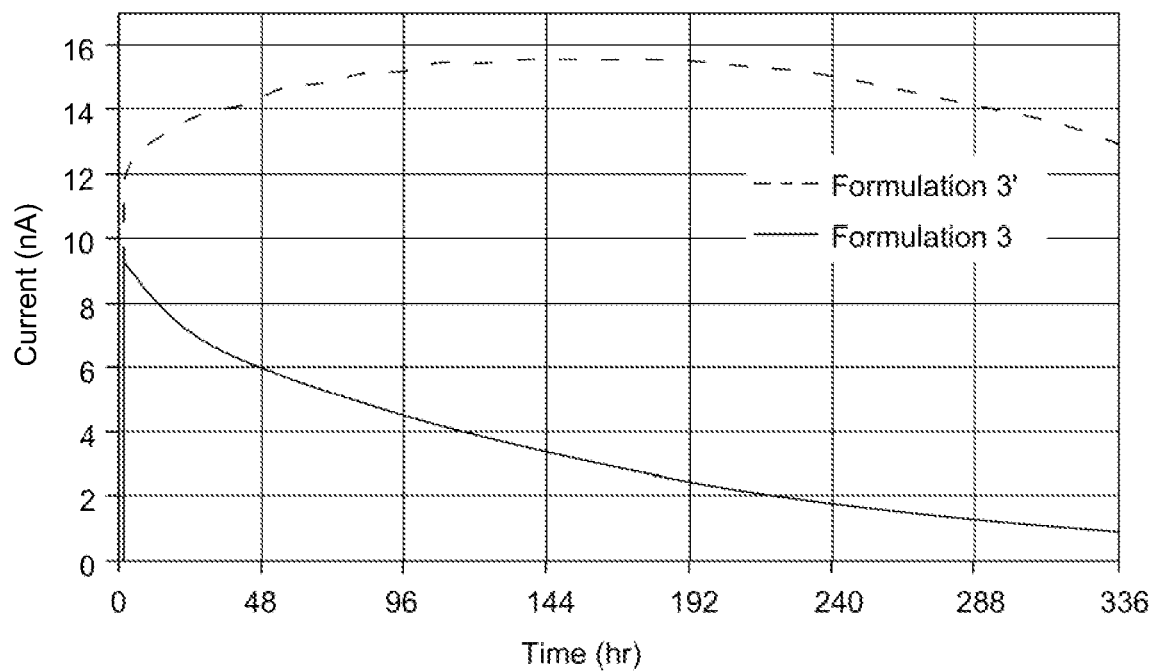
FIG. 5 shows an illustrative plot of comparative sensor performance for mass transport limiting membranes deposited from Formulations 3 and 3'.

FIG. 5 shows an illustrative plot of comparative performance for a lactate sensor containing an active area containing human serum albumin that is overcoated with a mass transport limiting membrane deposited either from Formulation 3 or Formulation 3'. As shown in FIG. 5, the mass transport limiting membrane deposited from Formulation 3 led to poor response stability when overcoated upon an active area containing lactate oxidase and human serum albumin (corresponds to sensor Group 3 above-see FIG. 3). The PEGDGE-crosslinked variant of the mass transport limiting membrane (deposited using Formulation 3') also produced a sensor response that varied over time, although less so than that deposited using Formulation 3. In addition, the mass transport limiting membrane deposited from Formulation 3' resulted in a higher response sensitivity than that resulting from Formulation 3. In contrast, both of these mass transport limiting membranes afforded a stable sensor response in the presence of glucose as an analyte (data not shown).

Alternative Crosslinker in Formulation 4 (Formulation 4').

Formulation 4 was modified with an alternative crosslinker as specified in Table 7 below. The modified formulation is designated as Formulation 4' herein.

TABLE 7

Polyvinylpyridine Formulation in 80:20
Ethanol:HEPES Buffer-PEGDGE1000 Crosslinked
(Formulation 4')

| Component | Concentration (mg/mL) |
|---|---|
| Polyvinylpyridine | 94.2 |
| PEGDGE1000 crosslinker | 11.0 |
| polydimethylsiloxane | 0.3 |

Formulation 4' was prepared by combining 4.3 mL of the membrane polymer in 80:20 ethanol:HEPES buffer (100 mg/mL), 0.25 mL of PEGDGE1000 in 80:20 ethanol: HEPES buffer (200 mg/mL), and 0.0132 mL of aminopropyl-terminated polydimethylsiloxane (PDMS) in ethanol (100 mg/mL).

Figure 6:
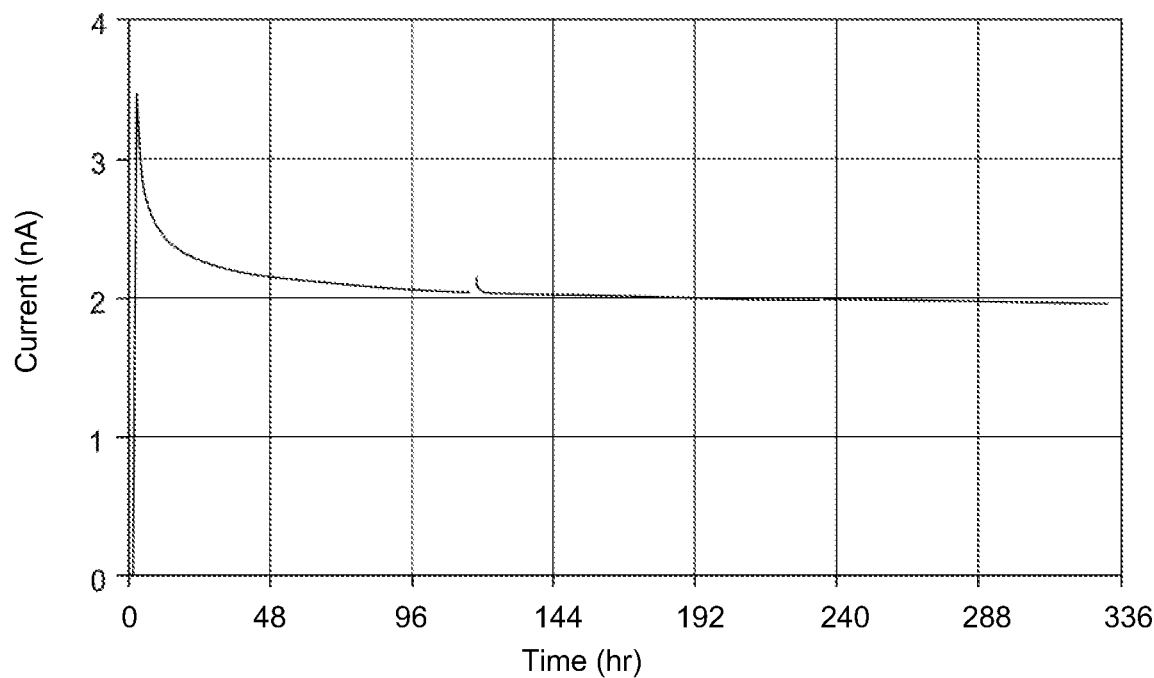
FIG. 6 shows an illustrative plot of sensor performance for a mass transport limiting membrane deposited from Formulation 4'.

FIG. 6 shows an illustrative plot of sensor performance for a mass transport limiting membrane deposited from Formulation 4'. Increasing the molecular weight of the crosslinker resulted in poorer sensor performance. As shown in FIG. 6, the mass transport limiting membrane resulting from Formulation 4' did not afford a stable current response over time. There was a large decrease in response over the first 48 hours, followed by relatively stable performance thereafter. In addition, the sensitivity was well below a target value of about 1 nA/mM.

Formulation 4' with Non-Crosslinked PEG Side Chains (Formulation 4").

Formulation 4' was modified to incorporate 3-4 wt. % non-crosslinked PEG side chains upon the PVP polymer backbone, which was then crosslinked with PEGDGE1000 as for Formulation 4' (designated as Formulation 4" herein). The composition of Formulation 4" is specified in Table 8 below.

TABLE 8

PEG-Functionalized Polyvinylpyridine Formulation in
80:20 Ethanol:HEPES Buffer-PEGDGE1000 Crosslinked
(Formulation 4")

| Component | Concentration (mg/mL) |
|---|---|
| PEG-Functionalized Polyvinylpyridine | 99.1 |
| PEGDGE1000 crosslinker | 1.2 |
| polydimethylsiloxane | 0.3 |

Formulation 4" was prepared by combining 4 mL of the membrane polymer in 80:20 ethanol:HEPES buffer (100 mg/mL), 0.025 mL of PEGDGE1000 in 80:20 ethanol: HEPES buffer (200 mg/mL), and 0.0132 mL of aminopropyl-terminated polydimethylsiloxane (PDMS) in ethanol (100 mg/mL).

Figure 7:
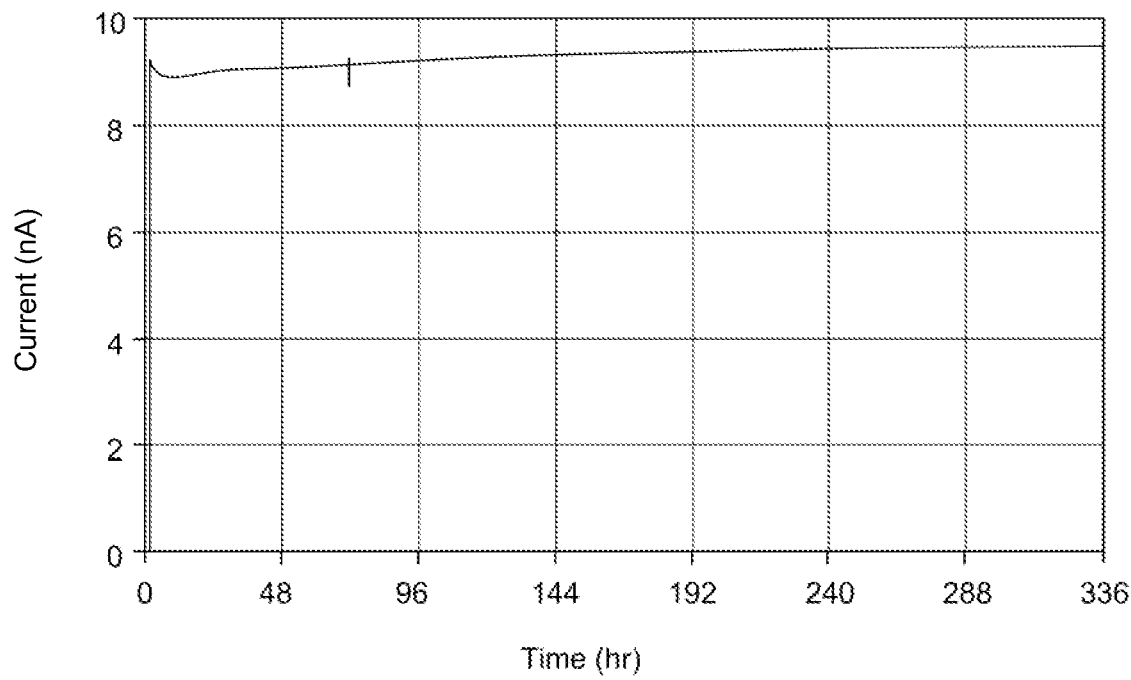
FIG. 7 shows an illustrative plot of sensor performance for a mass transport limiting membrane deposited from Formulation 4".
Figure 8:
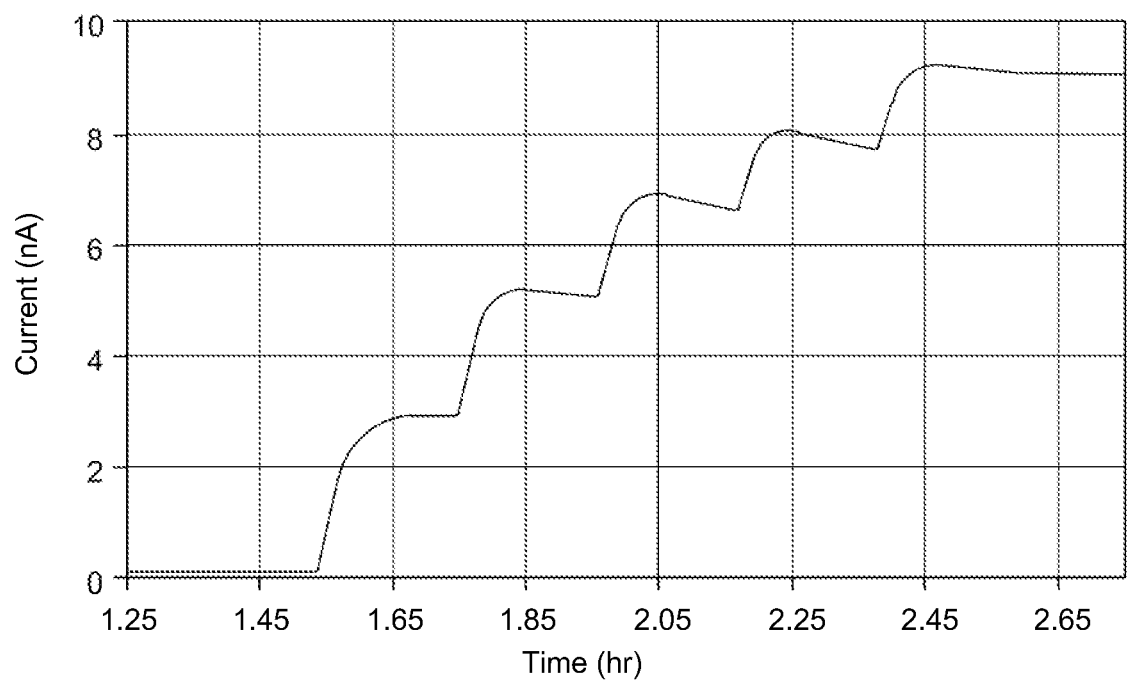
FIG. 8 shows an illustrative plot of sensor performance for a mass transport limiting membrane deposited from Formulation 4" to lactate solutions having varying lactate concentrations.

FIG. 7 shows an illustrative plot of sensor performance for a mass transport limiting membrane deposited from Formulation 4". As shown, the sensor responded rapidly and achieved a stable current at a value that was considerably greater than that provided by either Formulation 4 or Formulation 4'. Moreover, the sensor responded rapidly and achieved a stable current as increasing amounts of lactate were added in 1 mM increments (see FIG. 8). Thus, the sensor performance achieved with Formulation 4" demonstrates that crosslinkers other than PEGDGE400 may be used successfully as the crosslinking agent for the membrane polymer.

Bilayer Membrane Variants:

A bilayer mass transport limiting membrane was formed by depositing Formulation 4' upon the electrode surface, followed by deposition of the membrane polymer from Formulation 3' thereupon. As shown above, neither of these membrane polymers provided acceptable performance by themselves when overcoating an active area containing human serum albumin and lactate oxidase.

To prepare the sensor, the polymer from Formulation 4' was coated onto the electrode surface by repeated dip coating operations. Thereafter, the polymer from Formulation 3' was then coated onto the deposited crosslinked PVP layer by repeated dip coating operations. There was a 10 minute wait time between successive dips. After all dipping operations were complete, the sensors were cured at 25° C. for 24 hours, followed by 48 hours at 56° C. in dessicated vials.

Figure 9:
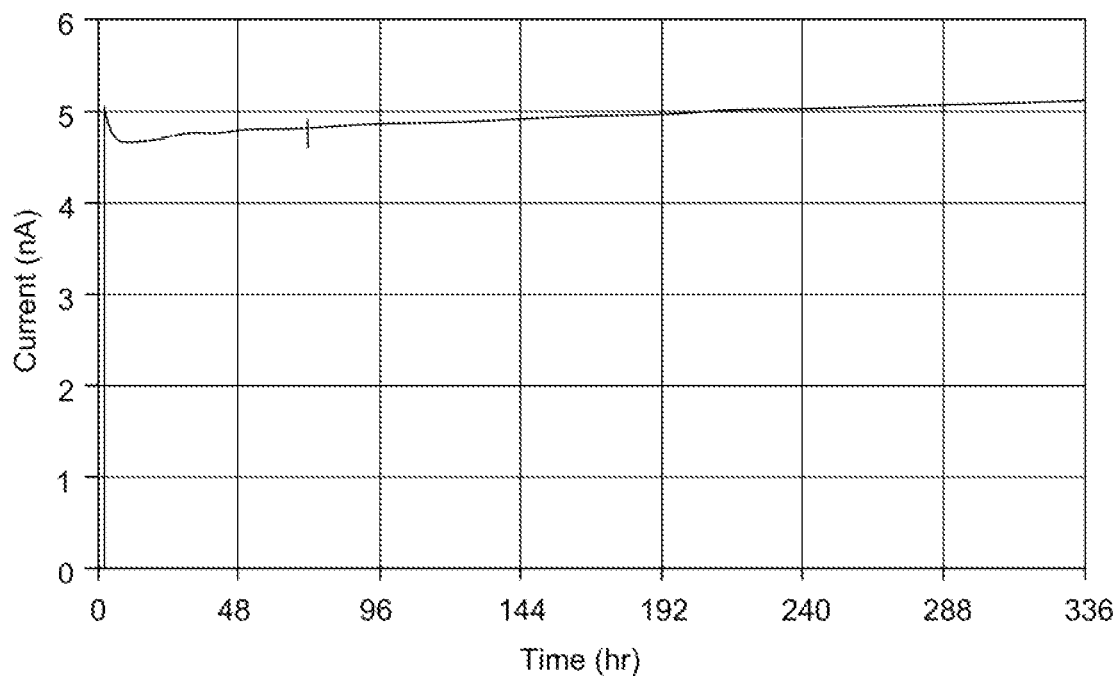
FIG. 9 shows an illustrative plot of sensor performance for a bilayer mass transport limiting membrane.

FIG. 9 shows an illustrative plot of sensor performance for a bilayer mass transport limiting membrane. As shown in FIG. 9, this bilayer construct surprisingly afforded a stable current response over time at an acceptable level of sensitivity, even though neither polymer provided acceptable performance alone. The response data in FIG. 9 was for an electrode that was dipped twice in Formulation 4' (crosslinked polyvinylpyridine) and then four times in Formulation 3' (crosslinked polyvinylpyridine-co-styrene)

Figure 10:
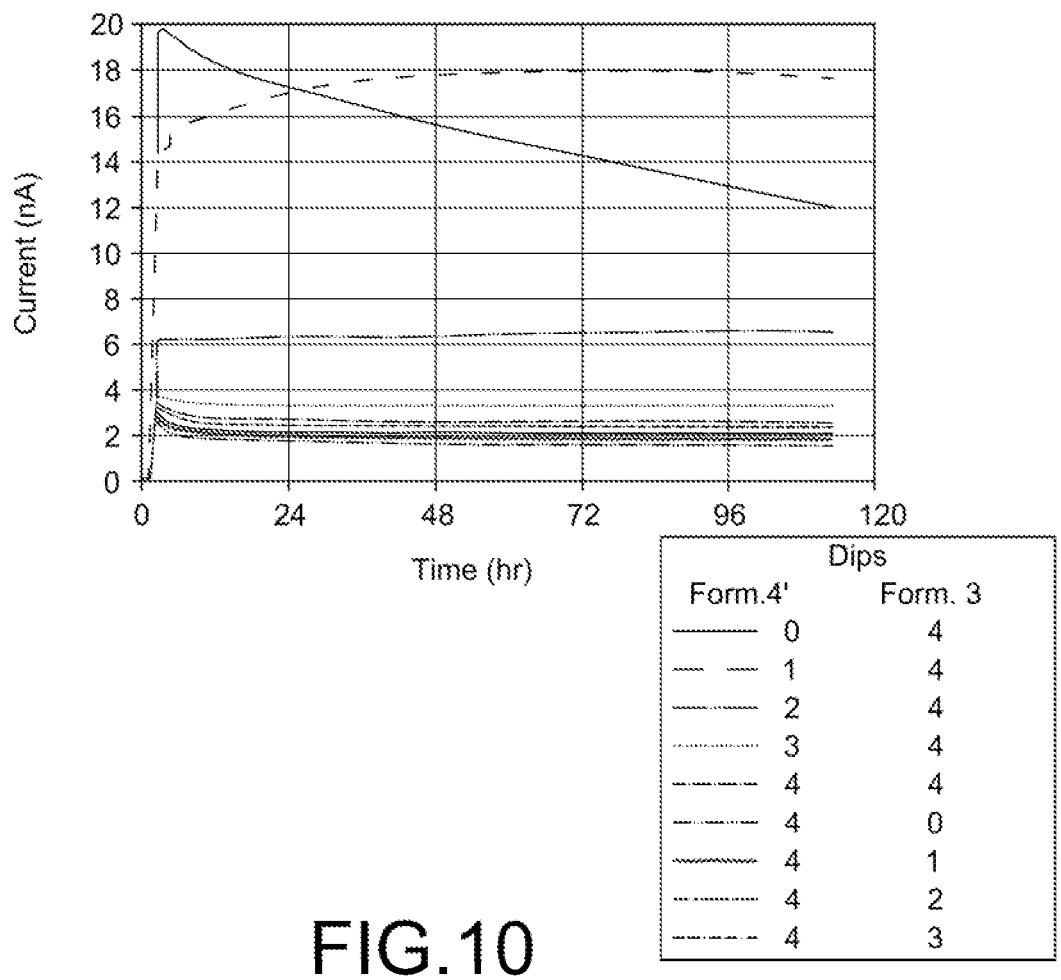
FIG. 10 shows an illustrative plot of sensor performance for bilayer mass transport limiting membranes having variable layer thicknesses.

The amount (thickness) of each membrane polymer in the bilayer mass transport limiting membrane may vary the sensor performance, as shown hereinafter in FIG. 10. FIG. 10 shows an illustrative plot of sensor performance for bilayer mass transport limiting membranes having variable layer thicknesses. Formulation 4' was used to deposit the lower layer in FIG. 10, and Formulation 3 (the Gly3-crosslinked variant of polyvinylpyridine-co-styrene) was used to deposit the upper layer. Thus, different crosslinkers are also tolerated for crosslinking the polyvinylpyridine-co-styrene polymer, even those that do not lead to acceptable performance when this polymer is used alone in a mass transport limiting membrane. As shown in FIG. 10, dip coating the electrode twice in Formulation 4' and four times in Formulation 3 afforded a good balance of sensitivity and a stable current response. Altering the number of dip coating operations changed the thickness of each component of the bilayer membrane, as well as the mass ratio of the membrane polymers to each other. As shown in FIG. 10, if the PVP layer is too thin (0 or 1 Formulation 4' dips), the sensitivity is high but the response stability is poor, whereas if it is too thick (3 or more dips), the electrode exhibits low sensitivity and poor response stability in some cases. Spray coating, screen printing, or similar processes may be alternately used to deposit the mass transport limiting membrane.

Admixed Membrane Variants:

A combined membrane formulation (Formulation 5) was prepared by mixing 1.5 mL of polyvinylpyridine in 80:20 ethanol:HEPES buffer (100 mg/mL), 2.5 mL of the polyvinylpyridine-co-styrene in 80:20 ethanol:HEPES buffer (140 mg/mL), 0.175 mL of PEGDGE400 in 80:20 ethanol: HEPES buffer (100 mg/mL), and 0.0132 mL of PDMS in ethanol (100 mg/mL). The composition of Formulation 7 is set forth below in Table 9.

TABLE 9

Polyvinylpyridine/Polyvinylpyridine-co-Styrene Formulation in
80:20 Ethanol:HEPES Buffer-PEGDGE400 Crosslinked
(Formulation 5)

| Component | Concentration (mg/mL) |
|---|---|
| Polyvinylpyridine | 35.8 |
| Polyvinylpyridine-co-styrene | 83.6 |
| PEGDGE400 crosslinker | 4.2 |
| polydimethylsiloxane | 0.3 |

Thus, after crosslinking Formulation 5 contained each of the polymers crosslinked with PEGDGE400.

Figure 11:
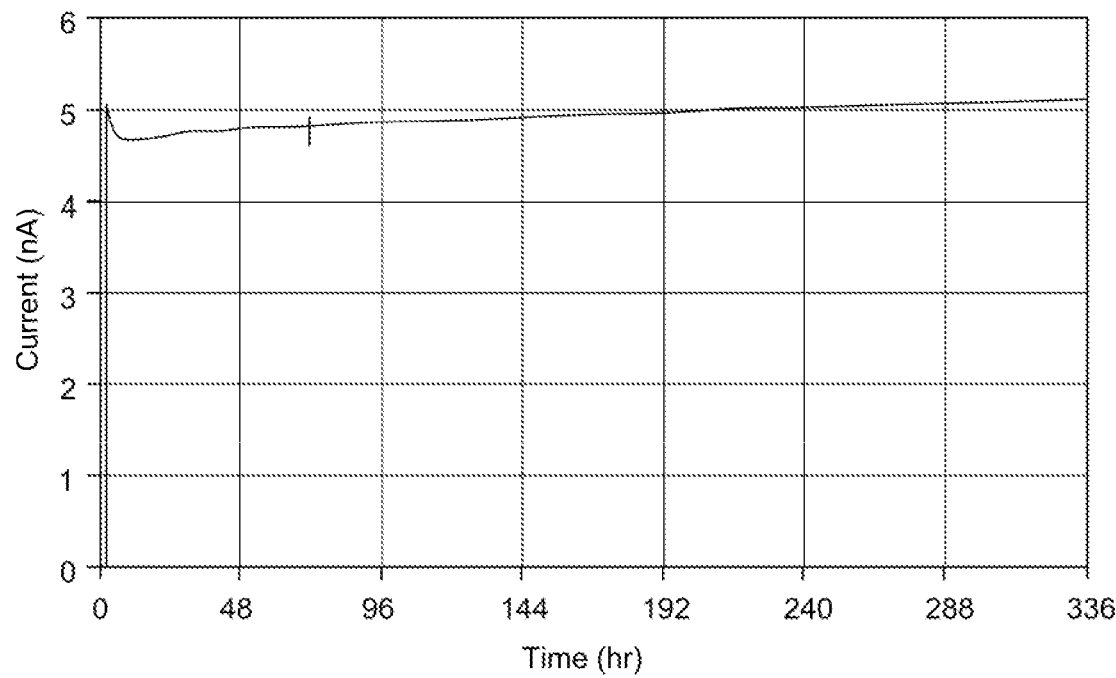
FIG. 11 shows an illustrative plot of sensor performance for an admixed mass transport limiting membrane.
Figure 12:
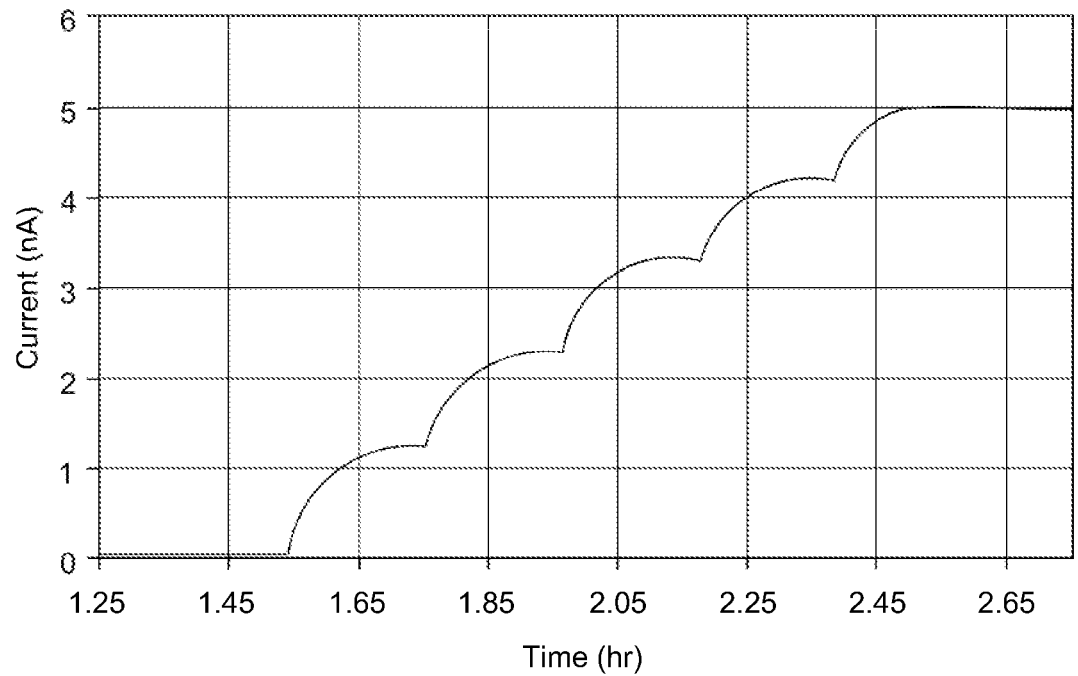
FIG. 12 shows an illustrative plot of sensor performance for an admixed mass transport limiting membrane to lactate solutions having varying lactate concentrations.

FIG. 11 shows an illustrative plot of sensor performance for an admixed mass transport limiting membrane. As shown, the admixed membrane afforded a stable current response over time and an acceptable level of sensitivity. Moreover, the current responded rapidly and achieved a stable value as increasing amounts of lactate were added in 1 mM increments (FIG. 12).

Figure 13:
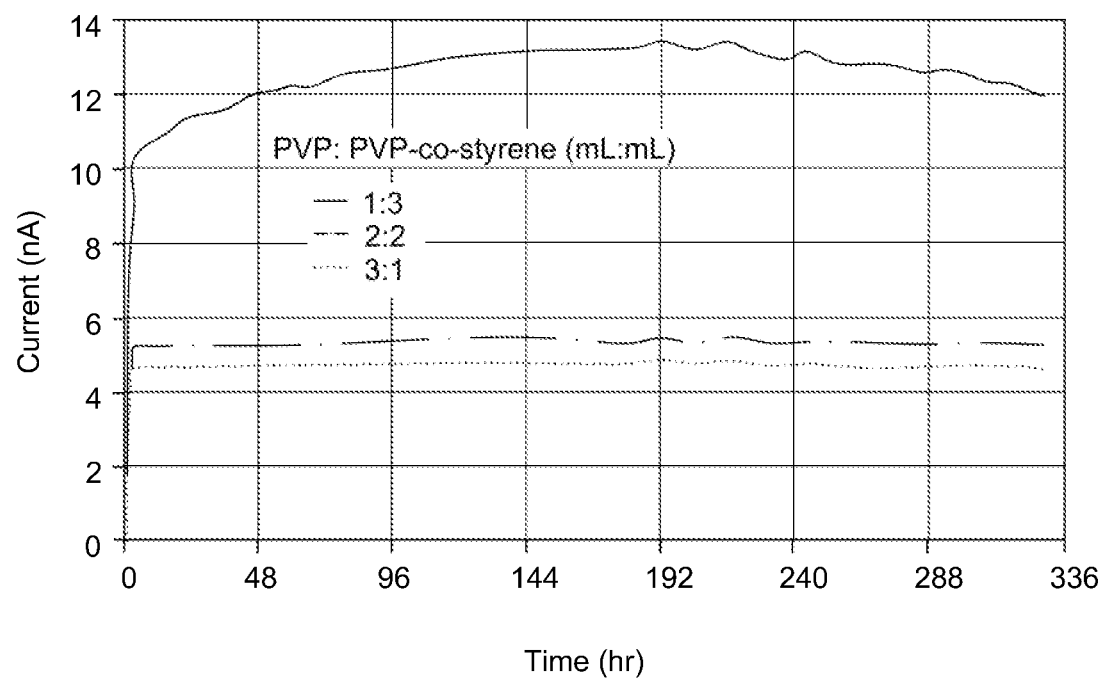
FIG. 13 shows an illustrative plot of sensor performance for an admixed mass transport limiting membrane having various ratios of crosslinked polyvinylpyridine to crosslinked polyvinylpyridine-co-styrene.

The admixed mass transport limiting membrane described above contained a 3:5 volume:volume ratio of the polyvinylpyridine to the polyvinylpyridine-co-styrene polymer. Alternative ratios of these two polymers also may produce acceptable performance. FIG. 13 shows an illustrative plot of sensor performance for an admixed mass transport limiting membrane having various ratios of crosslinked polyvinylpyridine to crosslinked polyvinylpyridine-co-styrene. As shown in FIG. 13, higher amounts of polyvinylpyridine also produced acceptable sensitivity and response stability. When the ratio of polyvinylpyridine to polyvinylpyridine-co-styrene was decreased from 2:2 volume:volume to 1:3 volume:volume, however, poorer response stability resulted, even though the overall sensitivity was higher.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A lactate sensor comprising:
   a working electrode having an active area disposed thereon, the active area comprising a polymer, human serum albumin, and a lactate-responsive enzyme covalently bonded to the polymer; and
   a mass transport limiting membrane overcoating at least the active area upon the working electrode, wherein the mass transport limiting membrane comprises a PEGDGE (polyethylene glycol diglycidyl ether)-crosslinked polyvinylpyridine homopolymer,
   wherein the albumin stabilizes the lactate responsive enzyme to provide a sensor signal that changes by 10% or less for at least 190 continuous hours at a given lactate concentration, and wherein the lactate-responsive enzyme and the human serum albumin are present in a weight ratio ranging from 5:1 to 1:1.

2. The lactate sensor of claim 1, wherein the lactate-responsive enzyme comprises lactate oxidase.

3. The lactate sensor of claim 1, wherein the active area comprises a plurality of sensing spots disposed upon the working electrode.

4. The lactate sensor of claim 1, wherein the mass transport limiting membrane comprises a multi-component membrane, the multi-component membrane comprising the PEGDGE-crosslinked polyvinylpyridine homopolymer and at least a second crosslinked polymer.

5. The lactate sensor of claim 4, wherein the multi-component membrane comprises a first polymer comprising the PEGDGE-crosslinked polyvinylpyridine homopolymer and a second polymer comprising a PEGDGE-crosslinked polyvinylpyridine copolymer.

6. The lactate sensor of claim 4, wherein the multi-component membrane comprises a bilayer membrane, the bilayer membrane comprising a first layer comprising the PEGDGE-polyvinylpyridine homopolymer and a second layer comprising the second crosslinked polymer.

7. The lactate sensor of claim 6, wherein the first layer is disposed directly upon the active area and the second layer is disposed upon the first layer.

8. The lactate sensor of claim 4, wherein the mass transport limiting membrane comprises a homogeneous admixture of the PEGDGE-crosslinked polyvinylpyridine homopolymer and the second crosslinked polymer.

9. The lactate sensor of claim 1, wherein the active area further comprises an electron transfer agent that is covalently bonded to the polymer.

10. A method comprising:
exposing the lactate sensor of claim 1 to a fluid;
obtaining the signal at or above an oxidation-reduction potential of the active area; and
correlating the signal to the lactate concentration in the fluid.

11. The method of claim 10, wherein the fluid is a biological fluid and the lactate sensor is exposed to the biological fluid in vivo.

12. The method of claim 10, wherein the lactate-responsive enzyme comprises lactate oxidase.

13. The method of claim 10, wherein the mass transport limiting membrane comprises at least the PEGDGE-crosslinked polyvinylpyridine homopolymer.

14. The method of claim 13, wherein the mass transport limiting membrane comprises a homogeneous admixture of the PEGDGE-crosslinked polyvinylpyridine homopolymer and the second crosslinked polymer.

15. The method of claim 10, wherein the mass transport limiting membrane comprises a multi-component membrane, the multi-component membrane comprising the PEGDGE-crosslinked polyvinylpyridine homopolymer and at least a second crosslinked polymer.

16. The method of claim 15, wherein the multi-component membrane comprises a first polymer comprising the PEGDGE-crosslinked polyvinylpyridine homopolymer and a second polymer comprising the PEGDGE-crosslinked polyvinylpyridine copolymer.

17. The method of claim 15, wherein the multi-component membrane comprises a bilayer membrane, the bilayer membrane comprising a first layer comprising the PEGDGE-polyvinylpyridine homopolymer and a second layer comprising the second crosslinked polymer.

18. The method of claim 17, wherein the first layer is disposed directly upon the active area and the second layer is disposed upon the first layer.

19. The method of claim 10, further comprising:
determining a presence of one or more conditions in a subject based upon the lactate concentration in the fluid, the one or more conditions being selected from the group consisting of sepsis, infection, organ function, and any combination thereof.

20. The method of claim 19, wherein the fluid is a biological fluid and the lactate sensor is exposed to the biological fluid in vivo.

21. The lactate sensor of claim 1, wherein the sensor generates a signal that is linearly proportional to a lactate concentration from 0 mM to 5 mM lactate.

22. The lactate sensor of claim 1, wherein the signal has an in vivo sensitivity of at least 1 nA/mM.

23. The lactate sensor of claim 1, wherein the sensor signal changes by 5% or less for at least 190 continuous hours at a given lactate concentration.

24. The lactate sensor of claim 1, wherein the sensor signal changes by 1% or less for at least 190 continuous hours at a given lactate concentration.

25. A lactate sensor comprising:
a working electrode having an active area disposed thereon, the active area comprising a polymer, human serum albumin, and a lactate-responsive enzyme covalently bonded to the polymer, and
a mass transport limiting membrane overcoating at least the active area upon the working electrode, wherein the mass transport limiting membrane comprises a PEGDGE (polyethylene glycol diglycidyl ether)-crosslinked polyvinylpyridine homopolymer,
wherein the lactate sensor is responsive to sepsis, infection, organ function, physiological stress, exercise, or any combination thereof and is configured to provide an alert or other indication that sepsis, infection, organ failure, or any combination thereof may be present for a measured lactate concentration,
wherein the lactate-responsive enzyme and the human serum albumin are present in a weight ratio ranging from 5:1 to 1:1, and
wherein the albumin stabilizes the lactate responsive enzyme to provide a sensor signal that changes by 10% or less for at least 190 continuous hours at a given lactate concentration.

26. The lactate sensor of claim 25, wherein the sensor generates a signal that is linearly proportional to a lactate concentration from 0 mM to 5 mM lactate.

27. The lactate sensor of claim 25, wherein the signal has an in vivo sensitivity of at least 1 nA/mM.

28. The lactate sensor of claim 25, wherein the sensor signal changes by 5% or less for at least 190 continuous hours at a given lactate concentration.

29. The lactate sensor of claim 25, wherein the sensor signal changes by 1% or less for at least 190 continuous hours at a given lactate concentration.

30. A lactate sensor comprising:
a working electrode having an active area disposed thereon, the active area comprising a polymer, a-human serum albumin, a lactate oxidase covalently bonded to the polymer, and an electron transfer agent that is covalently bonded to the polymer, and
a mass transport limiting membrane overcoating at least the active area upon the working electrode, wherein the albumin stabilizes the lactate responsive enzyme to provide a sensor signal that changes by 10% or less for at least 190 continuous hours at a given lactate concentration.

31. The lactate sensor of claim 30, wherein the sensor generates a signal that is linearly proportional to a lactate concentration from 0 mM to 5 mM lactate.

32. The lactate sensor of claim 30, wherein the signal has an in vivo sensitivity of at least 1 nA/mM.

33. The lactate sensor of claim 30, wherein the mass transport limiting membrane comprises a PEGDGE (polyethylene glycol diglycidyl ether)-crosslinked polyvinylpyridine homopolymer.

34. The lactate sensor of claim 30, wherein the sensor signal changes by 5% or less for at least 190 continuous hours at a given lactate concentration.

35. The lactate sensor of claim 30, wherein the sensor signal changes by 1% or less for at least 190 continuous hours at a given lactate concentration.

* * * * *